United States Patent
Daynard et al.

(10) Patent No.: US 8,884,034 B2
(45) Date of Patent: Nov. 11, 2014

(54) TOFA ANALOGS USEFUL IN TREATING DERMATOLOGICAL DISORDERS OR CONDITIONS

(75) Inventors: Timothy Scott Daynard, Vancouver (CA); Geoffrey C. Winters, Vancouver (CA); David W. C. Hunt, Surrey (CA)

(73) Assignee: Dermira (Canada), Inc., Redwood City, CA (US)

( * ) Notice: Subject to any disclaimer, the term of this patent is extended or adjusted under 35 U.S.C. 154(b) by 0 days.

(21) Appl. No.: 13/382,138

(22) PCT Filed: Jul. 1, 2010

(86) PCT No.: PCT/US2010/040795
§ 371 (c)(1),
(2), (4) Date: Apr. 24, 2012

(87) PCT Pub. No.: WO2011/005660
PCT Pub. Date: Jan. 13, 2011

(65) Prior Publication Data
US 2012/0208807 A1 Aug. 16, 2012

Related U.S. Application Data

(60) Provisional application No. 61/224,042, filed on Jul. 8, 2009.

(51) Int. Cl.
*C07D 307/58* (2006.01)
*A61K 31/341* (2006.01)
*C07D 307/68* (2006.01)
*C07D 405/12* (2006.01)
*C07D 407/12* (2006.01)

(52) U.S. Cl.
CPC ............ *C07D 307/68* (2013.01); *C07D 307/58* (2013.01); *C07D 405/12* (2013.01); *C07D 407/12* (2013.01); *A61K 31/341* (2013.01)
USPC .......................................... 549/479; 514/473

(58) Field of Classification Search
CPC ............................ C07D 307/58; A61K 31/341
USPC .......................................... 549/479; 514/473
See application file for complete search history.

(56) References Cited

U.S. PATENT DOCUMENTS

| | | |
|---|---|---|
| 4,093,622 A | 6/1978 | Henrick et al. |
| 4,110,351 A | 8/1978 | Parker |
| 4,146,623 A | 3/1979 | Parker |
| 4,935,421 A | 6/1990 | Kam et al. |
| 5,034,385 A | 7/1991 | DiNinno et al. |
| 5,059,716 A | 10/1991 | Joentgen et al. |
| 5,136,049 A | 8/1992 | Hanack et al. |
| 5,151,424 A | 9/1992 | Janssens et al. |
| 5,240,836 A | 8/1993 | Harper |
| 5,256,625 A | 10/1993 | Bussler et al. |
| 5,354,858 A | 10/1994 | Morgan et al. |
| 5,376,522 A | 12/1994 | Takiguchi et al. |
| 5,462,694 A | 10/1995 | Kosaka et al. |
| 5,462,941 A | 10/1995 | Iwase et al. |
| 5,470,586 A | 11/1995 | Gerhart |
| 5,512,596 A | 4/1996 | Kim et al. |
| 5,569,675 A | 10/1996 | Rephaeli et al. |
| 5,583,151 A | 12/1996 | Lunkenheimer et al. |
| 5,597,826 A | 1/1997 | Howard et al. |
| 5,653,913 A | 8/1997 | Nakamura et al. |
| 5,688,817 A | 11/1997 | Bernardon et al. |
| 5,698,581 A | 12/1997 | Kleemann et al. |
| 5,702,637 A | 12/1997 | Johnson et al. |
| 5,710,100 A | 1/1998 | Bussler et al. |
| 5,851,952 A | 12/1998 | Karp et al. |
| 5,869,426 A | 2/1999 | Karp et al. |
| 5,929,105 A | 7/1999 | Sternberg et al. |
| 5,977,395 A | 11/1999 | Boivin et al. |
| 5,993,690 A | 11/1999 | Kondo et al. |
| 5,998,499 A | 12/1999 | Klee et al. |
| 6,013,666 A | 1/2000 | Jew et al. |
| 6,090,807 A | 7/2000 | Hellendahl et al. |
| 6,139,924 A | 10/2000 | Keyes et al. |
| 6,309,561 B1 | 10/2001 | Hasegawa et al. |
| 6,333,082 B1 | 12/2001 | Duffy et al. |

(Continued)

FOREIGN PATENT DOCUMENTS

| | | |
|---|---|---|
| CN | 1073571 C | 10/2001 |
| CN | 101704700 A | 5/2010 |

(Continued)

OTHER PUBLICATIONS

Parker et al., "5-(Tetradecyloxy)-2-furancarboxylic Acid and Related Hypolipidemic Fatty Acid-Like Alkyloxyarylcarboxylic Acids," *J Med Chem* 20(6): 781-791, Jan. 1977.

*Primary Examiner* — Robert Havlin
(74) *Attorney, Agent, or Firm* — Seed IP Law Group PLLC

(57) ABSTRACT

This invention is directed to analogs of 5-(tetradecyloxy)-2-furancarboxylic acid (TOFA) and their use in the treatment of dermatological disorders or conditions characterized by sebaceous gland hyperactivity, such as acne and oily skin, and other dermatological disorders and conditions. This invention is also directed to pharmaceutical compositions comprising analogs of TOFA and a pharmaceutically acceptable excipient for dermatological or oral administration. Formula (I)

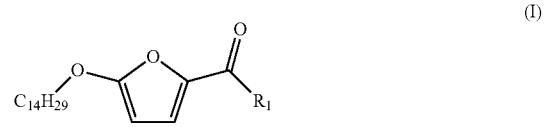

(I)

13 Claims, 3 Drawing Sheets

(56) References Cited

U.S. PATENT DOCUMENTS

| | | |
|---|---|---|
| 6,444,194 B1 | 9/2002 | Robinson et al. |
| 6,562,606 B1 | 5/2003 | Elias et al. |
| 6,579,882 B2 | 6/2003 | Stewart et al. |
| 6,589,914 B2 | 7/2003 | Sakamoto et al. |
| 6,600,951 B1 | 7/2003 | Anderson |
| 6,613,775 B1 | 9/2003 | Amin et al. |
| 6,733,690 B1 | 5/2004 | Lukac et al. |
| 6,777,412 B2 | 8/2004 | Clough et al. |
| 6,831,177 B1 | 12/2004 | Uenaka et al. |
| 6,887,700 B2 | 5/2005 | Popp et al. |
| 6,897,208 B2 | 5/2005 | Edwards et al. |
| 6,987,207 B1 | 1/2006 | Ronyak |
| 7,022,259 B2 | 4/2006 | Lee et al. |
| 7,022,857 B2 | 4/2006 | Meudt et al. |
| 7,153,549 B2 | 12/2006 | Spawn et al. |
| 7,154,114 B2 | 12/2006 | Brooks et al. |
| 7,179,946 B2 | 2/2007 | Scholz et al. |
| 7,262,204 B2 | 8/2007 | Collins et al. |
| 7,279,704 B2 | 10/2007 | Walters et al. |
| 7,297,168 B2 | 11/2007 | Murphy et al. |
| 7,317,034 B2 | 1/2008 | Sundermann et al. |
| 7,445,855 B2 | 11/2008 | Mackenzie et al. |
| 7,449,230 B2 | 11/2008 | Sabnis et al. |
| 7,491,823 B2 | 2/2009 | Thompson et al. |
| 7,531,558 B2 | 5/2009 | Macdonald et al. |
| 7,534,505 B2 | 5/2009 | Lin et al. |
| 7,534,547 B2 | 5/2009 | Hanabata et al. |
| 7,560,449 B2 | 7/2009 | Fine et al. |
| 7,649,104 B2 | 1/2010 | Fukuda et al. |
| 7,655,323 B2 | 2/2010 | Walters et al. |
| 7,659,307 B2 | 2/2010 | Gary et al. |
| 7,700,625 B2 | 4/2010 | Chessari et al. |
| 7,709,677 B2 | 5/2010 | Cooke et al. |
| 7,790,935 B2 | 9/2010 | Nagarajan et al. |
| 7,795,430 B2 | 9/2010 | Walters et al. |
| 7,828,992 B2 | 11/2010 | Kilickiran et al. |
| 7,834,180 B2 | 11/2010 | Chua et al. |
| 7,847,101 B2 | 12/2010 | Zhang et al. |
| 7,858,126 B2 | 12/2010 | Singh et al. |
| 7,956,192 B2 | 6/2011 | Tsai et al. |
| 7,964,742 B2 | 6/2011 | Nagarajan et al. |
| 8,007,926 B2 | 8/2011 | Thompson et al. |
| 8,038,902 B2 | 10/2011 | Kilickiran et al. |
| 8,114,533 B2 | 2/2012 | Djurovich et al. |
| 8,119,684 B2 | 2/2012 | Yeh et al. |
| 8,288,425 B2 | 10/2012 | Edwards et al. |
| 8,324,420 B2 | 12/2012 | Fukuda et al. |
| 2004/0092515 A1 | 5/2004 | Lundstedt et al. |
| 2004/0127499 A1 | 7/2004 | Pevear et al. |
| 2004/0131568 A1 | 7/2004 | Hwang et al. |
| 2005/0049242 A1 | 3/2005 | Robinson, Jr. et al. |
| 2005/0123667 A1 | 6/2005 | Sakuma et al. |
| 2005/0171350 A1 | 8/2005 | Take et al. |
| 2005/0198745 A1 | 9/2005 | Murphy et al. |
| 2005/0250794 A1 | 11/2005 | Napper et al. |
| 2006/0019952 A1 | 1/2006 | Distefano et al. |
| 2006/0078594 A1 | 4/2006 | Abrahamse et al. |
| 2006/0089410 A1 | 4/2006 | Bucalo et al. |
| 2006/0131762 A1 | 6/2006 | Meudt et al. |
| 2008/0027044 A1 | 1/2008 | Lewis et al. |
| 2008/0039633 A1 | 2/2008 | Jung et al. |
| 2008/0221350 A1 | 9/2008 | Meudt et al. |
| 2008/0311076 A1 | 12/2008 | Spencer et al. |
| 2009/0170924 A1 | 7/2009 | Mansfield et al. |
| 2009/0203913 A1 | 8/2009 | Deng et al. |
| 2010/0056780 A1 | 3/2010 | Jeong et al. |
| 2010/0056982 A1 | 3/2010 | Curaudeau et al. |
| 2010/0076028 A1 | 3/2010 | Wu et al. |
| 2010/0087494 A1 | 4/2010 | Coqueron et al. |
| 2010/0099726 A1 | 4/2010 | Cantley et al. |
| 2010/0210837 A1 | 8/2010 | Mahmud |
| 2010/0216786 A1 | 8/2010 | Susan et al. |
| 2010/0305121 A1 | 12/2010 | Smith et al. |
| 2010/0311930 A1 | 12/2010 | Sirol |
| 2011/0009438 A1 | 1/2011 | Mita et al. |
| 2011/0021771 A1 | 1/2011 | Mallais et al. |
| 2011/0028714 A1 | 2/2011 | Green et al. |
| 2011/0046142 A1 | 2/2011 | Lewis et al. |
| 2011/0053941 A1 | 3/2011 | Mautino et al. |
| 2011/0152290 A1 | 6/2011 | Schaefer et al. |
| 2011/0155962 A1 | 6/2011 | Choi |
| 2013/0030049 A1 | 1/2013 | Hunt et al. |

FOREIGN PATENT DOCUMENTS

| | | |
|---|---|---|
| CN | 101857622 A | 10/2010 |
| CN | 102134180 A | 7/2011 |
| DE | 40 33 563 A1 | 4/1992 |
| DE | 197 17 898 A1 | 10/1998 |
| DE | 197 18 742 A1 | 11/1998 |
| EP | 0 081 384 B1 | 4/1986 |
| EP | 0 356 944 A1 | 3/1990 |
| EP | 0 358 177 A1 | 3/1990 |
| EP | 0 402 269 A1 | 12/1990 |
| EP | 0 434 517 A3 | 10/1991 |
| EP | 0 552 085 A1 | 7/1993 |
| EP | 0 386 715 B1 | 2/1995 |
| FR | 2 831 537 A1 | 5/2003 |
| IN | 2003MU01287 A | 1/2006 |
| IN | 2010MU00587 A | 3/2010 |
| JP | 35002373 B | 3/1960 |
| JP | 11-43792 A | 6/1989 |
| JP | 3-101679 A | 4/1991 |
| JP | 3-197441 A | 8/1991 |
| JP | 3-266828 A | 11/1991 |
| JP | 4-29969 A | 1/1992 |
| JP | 4-67032 A | 3/1992 |
| JP | 8-59611 A | 3/1996 |
| JP | 10-287654 A | 10/1998 |
| JP | 2002-60658 A | 2/2002 |
| JP | 2002-363123 A | 12/2002 |
| JP | 2003-55367 A | 2/2003 |
| JP | 2004-107271 A | 4/2004 |
| JP | 2004-238298 A | 8/2004 |
| JP | 2004-315513 A | 11/2004 |
| JP | 2005-350527 A | 12/2005 |
| JP | 2007-223908 A | 9/2007 |
| JP | 4048645 B2 | 2/2008 |
| JP | 2010-235590 A | 10/2010 |
| KR | 876047 B1 | 12/2008 |
| RU | 2319694 C1 | 3/2008 |
| WO | WO 98/17253 A1 | 4/1998 |
| WO | 99/24427 A1 | 5/1999 |
| WO | 99/40088 A1 | 8/1999 |
| WO | 99/48371 A1 | 9/1999 |
| WO | 00/33836 A1 | 6/2000 |
| WO | 00/45799 A3 | 8/2000 |
| WO | 00/47578 A1 | 8/2000 |
| WO | 00/71118 A1 | 11/2000 |
| WO | 01/00590 A1 | 1/2001 |
| WO | 03/031401 A1 | 4/2003 |
| WO | 03/035065 A1 | 5/2003 |
| WO | 2004/024663 A1 | 3/2004 |
| WO | 2004/043457 A1 | 5/2004 |
| WO | 2004/061085 A2 | 7/2004 |
| WO | 2004/113258 A1 | 12/2004 |
| WO | WO 2004/111199 A2 | 12/2004 |
| WO | WO 2005/070126 A2 | 8/2005 |
| WO | 2005/113704 A3 | 12/2005 |
| WO | 2005/123667 A1 | 12/2005 |
| WO | 2006/100479 A1 | 9/2006 |
| WO | 2006/127569 A3 | 11/2006 |
| WO | 2008/003746 A1 | 1/2008 |
| WO | WO 2008/058034 A1 | 5/2008 |
| WO | 2009/019005 A3 | 2/2009 |
| WO | 2009/019015 A1 | 2/2009 |
| WO | 2009/023059 A3 | 2/2009 |
| WO | 2011/005660 A1 | 1/2011 |
| WO | 2011/053948 A1 | 5/2011 |
| WO | 2012/097264 A3 | 7/2011 |
| WO | 2011/092187 A1 | 8/2011 |

TOFA ANALOGS USEFUL IN TREATING DERMATOLOGICAL DISORDERS OR CONDITIONS

CROSS REFERENCE TO RELATED APPLICATION

This application claims the benefit under 35 U.S.C. 119(e) of U.S. Provisional Patent Application No. 61/224,042, filed Jul. 8, 2009, which is incorporated by reference in its entirety.

FIELD OF THE INVENTION

This invention is directed to the use of analogs of 5-(tetradecyloxy)-2-furancarboxylic acid (TOFA) for the treatment of dermatological disorders or conditions characterized by sebaceous gland hyperactivity, such as acne and oily skin. This invention is also directed to pharmaceutical and dermatological compositions comprising analogs of TOFA for use in treating dermatological disorders or conditions characterized by sebaceous gland hyperactivity, such as acne and oily skin.

BACKGROUND OF THE INVENTION

Hyperactive sebaceous gland disorders, such as acne vulgaris (acne), are common dermatological conditions affecting many people. Acne typically presents at the onset of puberty and peaks in incidence between 14 and 19 years of age. The prevalence of acne is greatly reduced by the middle of the third decade of life. Acne pathogenesis is multi-factorial involving sebaceous gland hyperactivity (increased production of sebum) with seborrhea, abnormal keratinocyte proliferation/desquamation and bacterial colonization promoting local inflammatory changes. As a consequence of the surge in androgen production at puberty, increased sebum production occurs along with abnormal desquamation of the epithelial lining of hair follicles. This mixture of sebum and cell debris is the basic ingredient of the comedone providing an ideal environment for the growth of *Propionibacterium acnes* (*P. acnes*), an anaerobic gram-positive bacterium that is part of normal skin flora and a key contributor to inflammatory acne. Bacterial-derived chemotactic factors and pro-inflammatory mediators subsequently foster local inflammatory reactions.

The clinical presentation of acne ranges from open comedones (whiteheads) and closed comedones (blackheads) for mild acne to the papules, pustules, nodules and cystic or mixed lesions for severe, inflammatory acne. Acne lesions typically occur on the face, upper back, chest and upper arms. The clinical course of acne tends to wax and wane. The severity of the condition is affected by multiple factors including seasonal and psychological influences as well as self-induced trauma by patients who habitually manipulate their lesions. Although generally transitory in course, moderate to severe inflammatory acne presents a true disease state that may cause long-term consequences for the subject including, but not limited to, socially disabling psychological damage and disfiguring physical scars.

A wide array of therapies for treating from moderate to severe acne is available. These therapies may affect specific aspects of the condition or in some cases affect several pathogenic factors. However, there are significant deficiencies in the currently available therapies for acne. Dermatological therapies are not fully effective against mild to moderate acne and many of the agents employed in these therapies produce skin irritation. Therapies employing dermatological retinoids and benzoyl peroxide are effective against mild to moderate acne by removing comedones, killing bacteria and/or reducing inflammation. Therapies employing antibiotics, given either dermatologically or orally, may be used to treat mild to moderate acne through the antibiotics' bacteriostatic and anti-inflammatory activities. Oral antibiotics do not typically produce satisfactory lesion clearance. In general, oral antibiotics used in the treatment of acne are slow-acting and require a treatment period of 3-6 months for optimum results. Hence compliance may be difficult, especially among younger patients. Long-term use of antibiotics is also associated with the spectre of bacterial antibiotic-resistance. Light-based therapies, such as 420-nm blue light or 1450-nm thermal lasers, can be used to treat mild to moderate acne based on their respective anti-bacterial photodynamic or thermal effect on sebaceous glands.

With current guidelines, the treatment regimen of choice for individuals with moderate to severe acne is oral antibiotics in combination with a dermatological agent such as a retinoid. For patients with recalcitrant nodular acne, first line therapy may consist of an oral retinoid, such as Accutane® (13-cis-retinoic acid). Accutane® has a strong inhibitory action on sebaceous glands and is therefore useful in removing comedones, reducing inflammation and inhibiting proliferation, differentiation and lipogenesis within sebaceous glands. In addition, Accutane® is also used to treat moderate or severe acne in patients at risk of physical or psychological scarring. Accutane® has long history of proven efficacy in treating acne. The majority of individuals treated with Accutane® experience remission with 3-6 months of daily dosing. In some cases, the treatment produces long-lasting benefit and is potentially curative. On the other hand, Accutane® is a recognized teratogen and is known to produce significant systemic adverse effects including elevated risk of mental depression, increased blood lipid levels and deleterious mucocutaneous changes. The strong inhibitory action of Accutane® on sebaceous gland activity clearly distinguishes it from the effects of dermatological retinoids and dermatological/oral antibiotics. However, topical treatment of acne is still preferred since this approach minimizes the risk of deleterious systemic effects associated with Accutane®. Drugs like Accutane®, which are effective orally, may have substantially less activity when administered topically, potentially due to their limited penetration into the skin and/or sebaceous glands.

Reducing sebum production as a means to treat acne has also been described. See, e.g., Zouboulis, C. C. et al., "Zileuton, an oral 5-lipoxygenase inhibitor, directly reduces sebum production", *Dermatology* (2005), Vol. 210, pp. 36-38; and Zouboulis, C. C. et al., "A new concept for acne therapy: a pilot study with zileuton, an oral 5-lipoxygenase inhibitor", *Arch. Dermatol.* (2003), Vol. 139, pp. 668-670. Zileuton, an orally active inhibitor of 5-lipoxygenase, the enzyme that catalyzes the formation of leukotriene B4 (LTB4) from arachidonic acid, was tested on moderate to severe acne patients. LTB4 promotes production of sebum lipids. The results of this study revealed a 65% reduction of sebum lipids and a 71% reduction in inflammatory lesions at 12 weeks. This work indicated that acne could significantly improve with a non-retinoid that acts by inhibiting sebum production.

There exists a need, therefore, for a fast-acting, effective and safe dermatological or oral therapy for acne and other dermatological disorders which are characterized by sebaceous gland hyperactivity.

SUMMARY OF THE INVENTION

Described herein are analogs of 5-(tetradecyloxy)-2-furancarboxylic acid (TOFA) and methods for using the analogs for the treatment of dermatological disorders or conditions characterized by sebaceous gland hyperactivity, such as acne vulgaris, acne conglobata, choracne, rosacea, Rhinophyma-type rosacea, seborrhea, seborrheic dermatitis, sebaceous gland hyperplasia, Meibomian gland dysfunction of facial rosacea, mitogenic alopecia, and oily skin.

Accordingly, in one aspect, this invention is directed to compounds of formula (I):

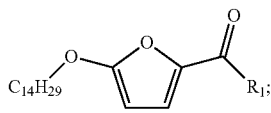

wherein:
$R^1$ is —O—$R^2$, —O—$R^3$—O$R^2$, —O—$R^3$—OC(O)—N($R^5$)$R^6$, —O—$R^3$—N($R^5$)$R^6$, —O—$R^3$—N($R^4$)C(O)O$R^5$, —O—$R^3$—C(O)O$R^5$, —O—$R^3$—C(O)N($R^5$)$R^6$ or —N($R^5$)S(O)$_2$—$R^4$;

each $R^2$ is independently alkyl, haloalkyl, optionally substituted aryl, optionally substituted aralkyl, optionally substituted heterocyclyl, optionally substituted heterocyclylalkyl, optionally substituted heteroaryl or optionally substituted substituted heteroarylalkyl;

each $R^3$ is independently an optionally substituted alkylene chain; and $R^4$ is optionally substituted alkyl, optionally substituted aryl, optionally substituted aralkyl, optionally substituted heteroaryl or optionally substituted heteroarylalkyl;

each $R^5$ is independently hydrogen, alkyl, optionally substituted cycloalkyl, optionally substituted aryl or optionally substituted aralkyl; and each $R^6$ is alkyl, optionally substituted cycloalkyl, optionally substituted aralkyl or —$R^3$—C(O)O$R^4$;

or any $R^5$ and $R^6$, together with the nitrogen to which they are both attached, form an optionally substituted N-heterocyclyl or an optionally substituted N-heteroaryl;

as a single stereoisomer or as a mixture thereof;
or a pharmaceutically acceptable salt thereof.

Another aspect of this invention is directed to a pharmaceutical composition comprising a therapeutically effective amount of a compound of formula (I), as set forth above, or a pharmaceutically acceptable salt thereof, and a pharmaceutically acceptable excipient.

In another aspect, this invention is directed to a method of treating a human having a dermatological disorder or condition characterized by sebaceous gland hyperactivity, wherein the method comprises administering to the human in need thereof a therapeutically effective amount of a compound of formula (I), as set forth above, or a pharmaceutically acceptable salt thereof.

In another aspect, this invention is directed to a method of treating a human having a dermatological disorder or condition characterized by sebaceous gland hyperactivity, wherein the method comprises administering to the human in need thereof a pharmaceutical composition comprising a therapeutically effective amount of a compound of formula (I), as set forth above, or a pharmaceutically acceptable salt thereof, and a pharmaceutically acceptable excipient.

Another aspect of this invention is directed to a method of inhibiting sebaceous gland activity in a human, wherein the method comprises administering to the human in need thereof a therapeutically effective amount of a compound of formula (I), as set forth above, or a pharmaceutically acceptable salt thereof.

Another aspect of this invention is directed to a method of inhibiting sebaceous gland activity in a human, wherein the method comprises administering to the human in need thereof a pharmaceutical composition comprising a therapeutically effective amount of a compound of formula (I), as set forth above, or a pharmaceutically acceptable salt thereof, and a pharmaceutically acceptable excipient.

Another aspect of this invention is directed to a method of treating a human having a disorder or condition characterized by inflammation, wherein the method comprises administering to the human in need thereof a pharmaceutical composition comprising a therapeutically effective amount of a compound of formula (I), as set forth above, or a pharmaceutically acceptable salt thereof, and a pharmaceutically acceptable excipient.

Another aspect of this invention is directed to a method of reducing T cell proliferation and cytokine secretion in a human having a disorder or condition characterized by inflammation, the method comprising administering to the human in need thereof a pharmaceutical composition comprising a therapeutically effective amount of a compound of formula (I), as set forth above, or a pharmaceutically acceptable salt thereof, and a pharmaceutically acceptable excipient.

Of the various aspects of the invention set forth above, it is understood that the compounds of formula (I) do not encompass compounds specifically disclosed or claimed in the following U.S. patents, the entire disclosures of which are incorporated in full by reference herein: U.S. Pat. No. 4,110,351; U.S. Pat. No. 4,146,623; U.S. Pat. No. 4,602,099; and U.S. Pat. No. 4,980,371. In a particular embodiment, the compounds of Formula (I) excludes 5-dodecyloxy-2-furoic acid, 5-tetradecyloxy-2-furoic acid methyl ester, 5-tetradecyloxy-2-furoic acid piperidinoethyl ester, and 5-tetradecyloxy-2-furoic acid 3-pyrrolidinyl ester.

The above aspects of the invention and embodiments thereof are described in more detail below.

DETAILED DESCRIPTION OF THE INVENTION

Definitions

Figure 1:
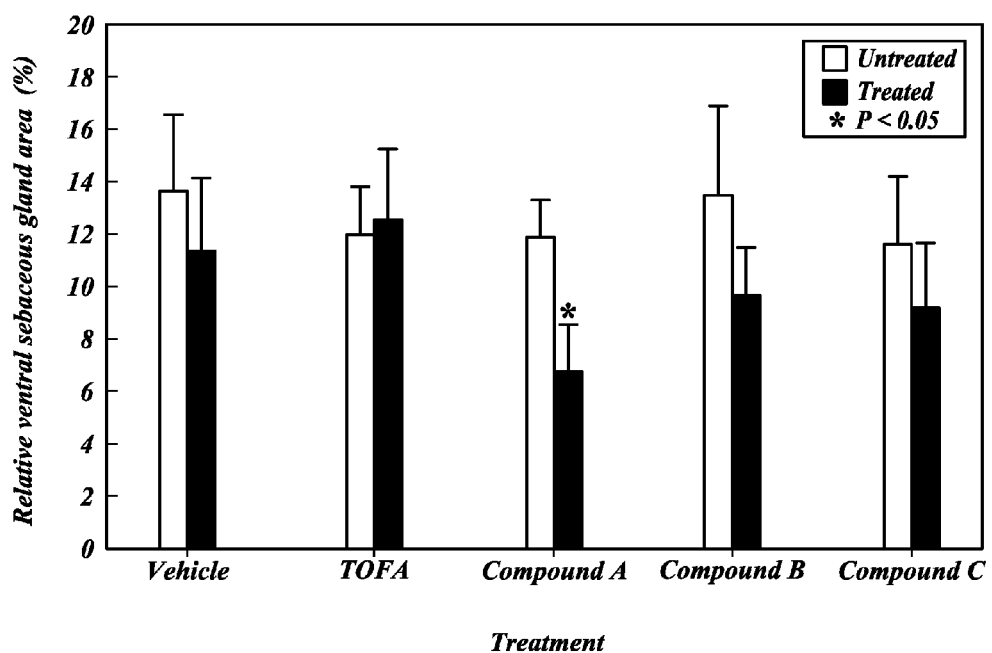
FIG. 1 provides the results of an in vivo assay to evaluate the effect of topical application of TOFA in parallel with three compounds of the invention on hamster ear sebaceous glands. Mean sebaceous gland counts with standard deviations (5 animals per group) for untreated and treated ears are shown. *P<0.05 by Students Test.

Certain chemical groups named herein may be preceded by a shorthand notation indicating the total number of carbon atoms that are to be found in the indicated chemical group.

For example; $C_7$-$C_{12}$alkyl describes an alkyl group, as defined below, having a total of 7 to 12 carbon atoms, and $C_4$-$C_{12}$cycloalkylalkyl describes a cycloalkylalkyl group, as defined below, having a total of 4 to 12 carbon atoms. The total number of carbons in the shorthand notation does not include carbons that may exist in substituents of the group described.

In addition to the foregoing, as used in the specification and appended claims, unless specified to the contrary, the following terms have the meaning indicated:

"Amino" refers to the —$NH_2$ radical.
"Cyano" refers to the —CN radical.
"Hydroxy" refers to the —OH radical.
"Imino" refers to the =NH substituent.
"Nitro" refers to the —$NO_2$ radical.
"Oxo" refers to the =O substituent.
"Thioxo" refers to the =S substituent.
"Trifluoromethyl" refers to the —$CF_3$ radical.

"Alkyl" refers to a straight or branched hydrocarbon chain radical consisting solely of carbon and hydrogen atoms, containing no unsaturation, having from one to twelve carbon atoms, preferably one to eight carbon atoms or one to six carbon atoms, and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, and the like. Unless stated otherwise specifically in the specification, an alkyl group may be optionally substituted by one of the following groups: alkyl, alkenyl, halo, haloalkenyl, cyano, nitro, aryl, cycloalkyl, heterocyclyl, heteroaryl, oxo, trimethylsilanyl, —$OR^{14}$, —OC(O)—$R^{14}$, —$N(R^{14})_2$, —$C(O)R^{14}$, —$C(O)OR^{14}$, —$C(O)N(R^{14})_2$, —$N(R^{14})C(O)OR^{16}$, —$N(R^{14})C(O)R^{16}$, —$N(R^{14})S(O)_tR^{16}$ (where t is 1 to 2), —$S(O)_tOR^{16}$ (where t is 1 to 2), —$S(O)_pR^{16}$ (where p is 0 to 2), and —$S(O)_tN(R^{14})_2$ (where t is 1 to 2) where each $R^{14}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each $R^{16}$ is alkyl, haloalkyl, cycloalkyl, cycloalkylalkyl, aryl, aralkyl, heterocyclyl, heterocyclylalkyl, heteroaryl or heteroarylalkyl.

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, e.g., methylene, ethylene, propylene, n-butylene, and the like. The alkylene chain is attached to the rest of the molecule through a single bond and to the radical group through a single bond. The points of attachment of the alkylene chain to the rest of the molecule and to the radical group can be through one carbon or any two carbons within the chain. Unless stated otherwise specifically in the specification, an alkylene chain may be optionally substituted by one of the following groups: alkyl, alkenyl, halo, haloalkenyl, cyano, nitro, aryl, cycloalkyl, heterocyclyl, heteroaryl, oxo, trimethylsilanyl, —$OR^{14}$, —OC(O)—$R^{14}$, —$N(R^{14})_2$, —$C(O)R^{14}$, —$C(O)OR^{14}$, —$C(O)N(R^{14})_2$, —$N(R^{14})C(O)OR^{16}$, —$N(R^{14})C(O)R^{16}$, —$N(R^{14})S(O)_tR^{16}$ (where t is 1 to 2), —$S(O)_tOR^{16}$ (where t is 1 to 2), —$S(O)_pR^{16}$ (where p is 0 to 2), and —$S(O)_tN(R^{14})_2$ (where t is 1 to 2) where each $R^{14}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each $R^{16}$ is alkyl, haloalkyl, cycloalkyl, cycloalkylalkyl, aryl, aralkyl, heterocyclyl, heterocyclylalkyl, heteroaryl or heteroarylalkyl.

"Aryl" refers to a hydrocarbon ring system radical comprising hydrogen, 6 to 18 carbon atoms and at least one aromatic ring. For purposes of this invention, the aryl radical may be a monocyclic, bicyclic, tricyclic or tetracyclic ring system, which may included fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" or the prefix "ar-" (such as in "aralkyl") is meant to include aryl radicals optionally substituted by one or more substituents independently selected from the group consisting of alkyl, alkenyl, halo, haloalkyl, haloalkenyl, cyano, nitro, aryl, aralkyl, heteroaryl, heteroarylalkyl, —$R^{15}$—$OR^{14}$, —$R^{15}$—$OC(O)$—$R^{14}$, —$R^{15}$—$N(R^{14})_2$, —$R^{15}$—$C(O)R^{14}$, —$R^{15}$—$C(O)OR^{14}$, —$R^{15}$—$C(O)N(R^{14})_2$, —$R^{15}$—$N(R^{14})C(O)OR^{16}$, —$R^{15}$—$N(R^{14})C(O)R^{16}$, —$R^{15}$—$N(R^{14})S(O)_tR^{16}$ (where t is 1 to 2), —$R^{15}$—$N=C(OR^{14})R^{14}$, —$R^{15}$—$S(O)_tOR^{16}$ (where t is 1 to 2), —$R^{15}$—$S(O)_pR^{16}$ (where p is 0 to 2), and —$R^{15}$—$S(O)_tN(R^{14})_2$ (where t is 1 to 2) where each $R^{14}$ is independently hydrogen, alkyl, haloalkyl, cycloalkyl, cycloalkylalkyl, aryl, aralkyl, heterocyclyl, heterocyclylalkyl, heteroaryl or heteroarylalkyl; each $R^{15}$ is independently a direct bond or a straight or branched alkylene or alkenylene chain; and each $R^{16}$ is alkyl, haloalkyl, cycloalkyl, cycloalkylalkyl, aryl, aralkyl, heterocyclyl, heterocyclylalkyl, heteroaryl or heteroarylalkyl.

"Aralkyl" refers to a radical of the formula —$R_b$—$R_c$ where $R_b$ is an alkylene chain as defined above and $R_c$ is one or more aryl radicals as defined above, for example, benzyl, diphenylmethyl and the like. The alkylene chain part of the aralkyl radical may be optionally substituted as described above for an alkylene chain. The aryl part of the aralkyl radical may be optionally substituted as described above for an aryl group.

"Cycloalkyl" refers to a stable non-aromatic monocyclic or polycyclic hydrocarbon radical consisting solely of carbon and hydrogen atoms, which may include fused or bridged ring systems, having from three to fifteen carbon atoms, preferably having from three to ten carbon atoms, and which is saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, and the like. Unless otherwise stated specifically in the specification, the term "cycloalkyl" is meant to include cycloalkyl radicals which are optionally substituted by one or more substituents independently selected from the group consisting of alkyl, alkenyl, halo, haloalkyl, haloalkenyl, cyano, nitro, oxo, aryl, aralkyl, cycloalkyl, cycloalkylalkyl, heterocyclyl, heterocyclylalkyl, heteroaryl, heteroarylalkyl, —$R^{15}$—$OR^{14}$, —$R^{15}$—$OC(O)$—$R^{14}$, —$R^{15}$—$N(R^{14})_2$, —$R^{15}$—$C(O)R^{14}$, —$R^{15}$—$C(O)OR^{14}$, —$R^{15}$—$C(O)N(R^{14})_2$, —$R^{15}$—$N(R^{14})C(O)OR^{16}$, —$R^{15}$—$N(R^{14})C(O)R^{16}$, —$R^{15}$—$N(R^{14})S(O)_tR^{16}$ (where t is 1 to 2), —$R^{15}$—$N=C(OR^{14})R^{14}$, —$R^{15}$—$S(O)_tOR^{16}$ (where t is 1 to 2), —$R^{15}$—$S(O)_pR^{16}$ (where p is 0 to 2), and —$R^{15}$—$S(O)_tN(R^{14})_2$ (where t is 1 to 2) where each $R^{14}$ is independently hydrogen, alkyl, haloalkyl, cycloalkyl, cycloalkylalkyl, aryl, aralkyl, heterocyclyl, heterocyclylalkyl, heteroaryl or heteroarylalkyl; each $R^{15}$ is independently a direct bond or a straight or branched alkylene or alkenylene chain; and each $R^{16}$ is alkyl, haloalkyl, cycloalkyl, cycloalkylalkyl, aryl, aralkyl, heterocyclyl, heterocyclylalkyl, heteroaryl or heteroarylalkyl.

"Halo" refers to bromo, chloro, fluoro or iodo.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1-fluoromethyl-2-fluoroethyl, 3-bromo-2-fluoropropyl, 1-bromomethyl-2-bromoethyl, and the like. The alkyl part of the haloalkyl radical may be optionally substituted as defined above for an alkyl group.

"Heterocyclyl" refers to a stable 3- to 18-membered non-aromatic ring radical which consists of two to twelve carbon atoms and from one to six heteroatoms selected from the group consisting of nitrogen, oxygen and sulfur. Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxo-1,3-dioxol-4yl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocyclyl" is meant to include heterocyclyl radicals as defined above which are optionally substituted by one or more substituents selected from the group consisting of alkyl, alkenyl, halo, haloalkyl, haloalkenyl, cyano, oxo, thioxo, nitro, aryl, aralkyl, cycloalkyl, cycloalkylalkyl, heterocyclyl, heterocyclylalkyl, heteroaryl, heteroarylalkyl, $-R^{15}-OR^{14}$, $-R^{15}-OC(O)-R^{14}$, $-R^{15}-N(R^{14})_2$, $-R^{15}-C(O)R^{14}$, $-R^{15}-C(O)OR^{14}$, $-R^{15}-C(O)N(R^{14})_2$, $-R^{15}-N(R^{14})C(O)OR^{16}$, $-R^{15}-N(R^{14})C(O)R^{16}$, $-R^{15}-N(R^{14})S(O)_tR^{16}$ (where t is 1 to 2), $-R^{15}-N=C(OR^{14})R^{14}$, $-R^{15}-S(O)_tOR^{16}$ (where t is 1 to 2), $-R^{15}-S(O)_pR^{16}$ (where p is 0 to 2), and $-R^{15}-S(O)_tN(R^{14})_2$ (where t is 1 to 2) where each $R^{14}$ is independently hydrogen, alkyl, alkenyl, haloalkyl, cycloalkyl, cycloalkylalkyl, aryl, aralkyl, heterocyclyl, heterocyclylalkyl, heteroaryl or heteroarylalkyl; each $R^{15}$ is independently a direct bond or a straight or branched alkylene or alkenylene chain; and each $R^{16}$ is alkyl, alkenyl, haloalkyl, cycloalkyl, cycloalkylalkyl, aryl, aralkyl, heterocyclyl, heterocyclylalkyl, heteroaryl or heteroarylalkyl.

"N-heterocyclyl" refers to a heterocyclyl radical as defined above containing at least one nitrogen and where the point of attachment of the heterocyclyl radical to the rest of the molecule is through a nitrogen atom in the heterocyclyl radical. An N-heterocyclyl radical may be optionally substituted as described above for heterocyclyl radicals.

"Heterocyclylalkyl" refers to a radical of the formula $-R_bR_h$ where $R_b$ is an alkylene chain as defined above and $R_h$ is a heterocyclyl radical as defined above, and if the heterocyclyl is a nitrogen-containing heterocyclyl, the heterocyclyl may be attached to the alkylene chain at the nitrogen atom. The alkylene chain of the heterocyclylalkyl radical may be optionally substituted as defined above for an alkylene chain. The heterocyclyl part of the heterocyclylalkyl radical may be optionally substituted as defined above for a heterocyclyl group.

"Heteroaryl" refers to a 5- to 14-membered ring system radical comprising hydrogen atoms, one to thirteen carbon atoms, one to six heteroatoms selected from the group consisting of nitrogen, oxygen and sulfur, and at least one aromatic ring. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzthiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, pyrrolyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl). Unless stated otherwise specifically in the specification, the term "heteroaryl" is meant to include heteroaryl radicals as defined above which are optionally substituted by one or more substituents selected from the group consisting of alkyl, alkenyl, alkoxy, halo, haloalkyl, haloalkenyl, cyano, oxo, thioxo, nitro, aryl, aralkyl, cycloalkyl, cycloalkylalkyl, heterocyclyl, heterocyclylalkyl, heteroaryl, heteroarylalkyl, $-R^{15}-OR^{14}$, $-R^{15}-OC(O)-R^{14}$, $-R^{15}-N(R^{14})_2$, $-R^{15}-C(O)R^{14}$, $-R^{15}-C(O)OR^{14}$, $-R^{15}-C(O)N(R^{14})_2$, $-R^{15}-N(R^{14})C(O)OR^{16}$, $-R^{15}-N(R^{14})C(O)R^{16}$, $-R^{15}-N(R^{14})S(O)_tR^{16}$ (where t is 1 to 2), $-R^{15}-N=C(OR^{14})R^{14}$, $-R^{15}-S(O)_tOR^{16}$ (where t is 1 to 2), $-R^{15}-S(O)_pR^{16}$ (where p is 0 to 2), and $-R^{15}-S(O)_tN(R^{14})_2$ (where t is 1 to 2) where each $R^{14}$ is independently hydrogen, alkyl, alkenyl, haloalkyl, cycloalkyl, cycloalkylalkyl, aryl, aralkyl, heterocyclyl, heterocyclylalkyl, heteroaryl or heteroarylalkyl; each $R^{15}$ is independently a direct bond or a straight or branched alkylene or alkenylene chain; and each $R^{16}$ is alkyl, alkenyl, haloalkyl, cycloalkyl, cycloalkylalkyl, aryl, aralkyl, heterocyclyl, heterocyclylalkyl, heteroaryl or heteroarylalkyl.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical may be optionally substituted as described above for heteroaryl radicals.

"Heteroarylalkyl" refers to a radical of the formula $-R_bR_i$ where $R_b$ is an alkylene chain as defined above and $R_i$ is a heteroaryl radical as defined above. The heteroaryl part of the heteroarylalkyl radical may be optionally substituted as defined above for a heteroaryl group. The alkylene chain part of the heteroarylalkyl radical may be optionally substituted as defined above for an alkylene chain.

"Dermatological disorder or conditions" includes disorders involving hyperactive sebaceous gland activity including, for example, acne vulgaris, acne conglobata, choracne, rosacea, Rhinophyma-type rosacea, seborrhea, seborrheic dermatitis, sebaceous gland hyperplasia, Meibomian gland dysfunction of facial rosacea, mitogenic alopecia, and oily skin.

"Dermatologically acceptable excipient" includes without limitation any adjuvant, carrier, vehicle, excipient, glidant, sweetening agent, diluent, preservative, dye/colorant, flavor enhancer, surfactant, wetting agent, dispersing agent, suspending agent, stabilizer, isotonic agent, solvent, or emulsifier, including those approved by the United States Food and Drug Administration as being acceptable for dermatological use on humans or domestic animals, or which are known, or are suitable for use in dermatological compositions.

As is known, the skin (especially stratum corneum) provides a physical barrier to the harmful effects of the external environment. In doing so, it also interferes with the absorption or transdermal delivery of topical therapeutic drugs. Thus, a suitable dermatologically acceptable excipient may include one or more penetration enhancers (or permeation enhancers), which are substances that promote the diffusion of the therapeutic drugs (e.g., the TOFA analogs described herein) through the skin barrier. They typically act to reduce the impedance or resistance of the skin to allow improved permeation of the therapeutic drugs. In particular, substances which would perturb the normal structure of the stratum corneum are capable of disrupting the intercellular lipid organization, thus reducing its effectiveness as a barrier. These substances could include any lipid material which would partition into the stratum corneum lipids causing a direct effect or any material which would effect the proteins and cause an indirect perturbation of the lipid structure. Furthermore, solvents, such as ethanol, can remove lipids from the stratum corneum, thus destroying its lipid organization and disrupting its barrier function.

Examples of penetration enhancers or barrier function disrupters include, but are not limited to, alcohol-based enhancers, such as alkanols with one to sixteen carbons, benzyl alcohol, butylene glycol, diethylene glycol, glycofurol, glycerides, glycerin, glycerol, phenethyl alcohol, polypropylene glycol, polyvinyl alcohol, and phenol; amide-based enhancers, such as N-butyl-N-dodecylacetamide, crotamiton, N,N-dimethylformamide, N,N-dimethylacetamide, N-methyl formamide, and urea; amino acids, such as L-α-amino acids and water soluble proteins; azone and azone-like compounds, such as azacycloalkanes; essential oils, such as almond oil, amyl butyrate, apricot kernel oil, avocado oil, camphor, castor oil, 1-carvone, coconut oil, corn oil, cotton seed oil, eugenol, menthol, oil of anise, oil of clove, orange oil, peanut oil, peppermint oil, rose oil, safflower oil, sesame oil, shark liver oil (squalene), soybean oil, sunflower oil, and walnut oil; vitamins and herbs, such as aloe, allantoin, black walnut extract, chamomile extract, panthenol, papain, tocopherol, and vitamin A palmitate; waxes, such as candelilla wax, carnuba wax, ceresin wax, beeswax, lanolin wax, jojoba oil, petrolatum; mixes, such as primary esters of fractionated vegetable oil fatty acids with glycerine or propylene glycol, and interesterified medium chain triglyceride oils; fatty acids and fatty acid esters, such as amyl caproate, butyl acetate, caprylic acid, cetyl ester, diethyl sebacate, dioctyl malate, elaidic acid ethyl caprylate, ethyl glycol palmitostearate, glyceryl beheate, glucose glutamate, isobutyl acetate, laureth-4, lauric acid, malic acid, methyl caprate, mineral oil, myristic acid, oleic acid, palmitic acid, PEG fatty esters, polyoxylene sorbitan monooleate, polypropylene glycols, propylene glycols, saccharose disterate, salicylic acid, sodium citrate, stearic acid, soaps, and caproic-, caprylic-, capric-, and lauric-triglycerides; macrocylics, such as butylated hydroxyanisole, cyclopentadecanolide, cyclodextrins; phospholipid and phosphate enhancers, such as dialkylphosphates, ditetradecyl phosphate, lecithin, 2-pyrrolidone derivatives, such as alkyl pyrrolidone-5-carboxylate esters, pyroglutamic acid esters, N-methyl pyrrolidone, biodegradable soft penetration enhancers, such as dioxane derivatives and dioxolane derivatives; sulphoxide enhancers, such as dimethyl sulphoxide and decylmethyl sulphoxide; acid enhancers, such as alginic acid, sorbic acid, and succinic acid; cyclic amines; imidazolinones; imidazoles; ketones, such as acetone, dimethicone, methyl ethyl ketone, and pentanedione; lanolin derivatives, such as lanolin alcohol, PEG 16 lanolin, and acetylated lanolin; oxazolines; oxazolindinones; proline esters; pyrroles, urethanes; and surfactants, such as nonoxynols, polysorbates, polyoxylene alcohols, polyoxylene fatty acid esters, sodium lauryl sulfate, and sorbitan monostearate.

"Dermatologically effective amount" refers to that amount of an active ingredient which, when administered dermatologically (i.e., systemically or locally, including, for example, topically, intradermally, intravenously, orally or by use of an implant, that afford administration to the sebaceous glands) to a human, is sufficient to effect the desired treatment, as defined below, of the disorder or condition of interest in the human. The amount of an active ingredient which constitutes a "dermatologically effective amount" will vary depending on the active ingredient, the disorder or condition and its severity, and the age of the human to be treated, but can be determined routinely by one of ordinary skill in the art having regard to his own knowledge and to this disclosure.

"Stable compound" and "stable structure" are meant to indicate a compound that is sufficiently robust to survive isolation to a useful degree of purity from a reaction mixture, and formulation into an efficacious therapeutic agent.

"Mammal" includes humans and both domestic animals such as laboratory animals and household pets, (e.g. cats, dogs, swine, cattle, sheep, goats, horses, rabbits), and non-domestic animals such as wildlife and the like.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution. When a functional group is described as "optionally substituted," and in turn, substitutents on the functional group are also "optionally substituted" and so on, for the purposes of this invention, such iterations are limited to five, preferably such iterations are limited to two.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

A "pharmaceutical composition" refers to a formulation of a compound of the invention and a medium generally accepted in the art for the delivery of the biologically active compound to mammals, e.g., humans. Such a medium includes all pharmaceutically acceptable carriers, diluents or excipients therefor.

"Therapeutically effective amount" refers to that amount of a compound of the invention which, when administered to a mammal, preferably a human, is sufficient to effect treatment of the disease or condition of interest in a mammal, preferably a human, having the disease or condition. The amount of a compound of the invention which constitutes a "therapeutically effective amount" will vary depending on the compound, the disease or condition and its severity, the manner of administration, and the age of the mammal to be treated, but can be determined routinely by one of ordinary skill in the art having regard to his own knowledge and to this disclosure. Preferably, for purposes of this invention, a "therapeutically effective amount" is that amount of a compound of invention which is sufficient to inhibit sebaceous gland activity.

"Treating" or "treatment", as used herein, covers the treatment of the disease or condition of interest in a mammal, preferably a human, and includes:

(i) preventing the disease or condition from occurring in the mammal;

(ii) inhibiting the disease or condition in the mammal, i.e., arresting its development;

(iii) relieving the disease or condition in the mammal, i.e., causing regression of the disease or condition; or (iv) relieving the symptoms of the disease or condition in the mammal, i.e., relieving the symptoms without addressing the underlying disease or condition; or As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The compounds of the invention, or their pharmaceutically acceptable salts may contain one or more asymmetric centres and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallisation. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centres of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

The chemical naming protocol and structure diagrams used herein are a modified form of the I.U.P.A.C. nomenclature system, using the ChemDraw Version 10 software naming program (CambridgeSoft). For complex chemical names employed herein, a substituent group is named before the group to which it attaches. For example, 2 cyclopropylethyl comprises an ethyl backbone with cyclopropyl substituent. In chemical structure diagrams, all bonds are identified, except for some carbon atoms, which are assumed to be bonded to sufficient hydrogen atoms to complete the valency.

The use of parentheses in substituent groups is used herein to conserve space. Accordingly, the use of parenthesis in a substituent group indicates that the group enclosed within the parentheses is attached directly to the atom preceding the parenthesis. For example, one of the choices for $R^1$ is the —O—$R^3$—OC(O)—N($R^5$)$R^6$ group. The formula for this group can be drawn as follows:

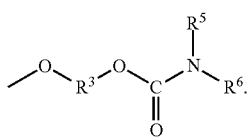

Thus, for example, a compound of formula (I) wherein $R^1$ 3-morpholinopropoxy; i.e., a compound of the following formula:

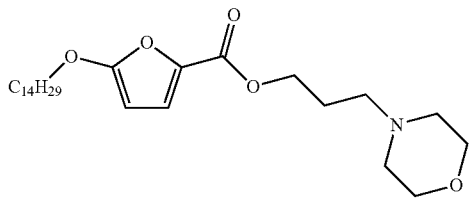

is named herein as 3-morpholinopropyl 5-(tetradecyloxy)furan-2-carboxylate.

Embodiments of the Invention

Of the various aspects of the invention set forth above in the Summary of the Invention, certain embodiments are preferred.

Of the compounds of formula (I), as set forth above in the Summary of the Invention, one embodiment is a compound of formula (I) wherein:
$R^1$ is —O—$R^2$; and
$R^2$ is independently alkyl or heterocyclylalkyl.
Of this embodiment, one embodiment is a compound of formula (I) selected from:
isopropyl 5-(tetradecyloxy)furan-2-carboxylate;
4-methylpentyl 5-(tetradecyloxy)furan-2-carboxylate; and
(5-methyl-2-oxo-1,3-dioxol-4-yl)methyl 5-(tetradecyloxy)furan-2-carboxylate.

Of the compounds of formula (I), as set forth above in the Summary of the Invention, another embodiment is a compound of formula (I) wherein:
$R^1$ is —O—$R^2$; and
$R^2$ is haloalkyl or substituted aryl.
Of this embodiment, one embodiment is a compound of formula (I) selected from:
2,2,2-trifluoroethyl 5-(tetradecyloxy)furan-2-carboxylate;
2,2,2-trichloroethyl 5-(tetradecyloxy)furan-2-carboxylate;
2-bromoethyl 5-(tetradecyloxy)furan-2-carboxylate; and
2-(5-(tetradecyloxy)furan-2-carbonyloxy)benzoic acid.

Of the compounds of formula (I), as set forth above in the Summary of the Invention, another embodiment is a compound of formula (I) wherein:
$R^1$ is —O—$R^3$—O$R^2$;
$R^2$ is optionally substituted heterocyclylalkyl; and
$R^3$ is an optionally substituted alkylene chain.
Of this embodiment, one embodiment is a compound of formula (I) which is 3-(tetrahydro-2H-pyran-2-yloxy)propyl 5-(tetradecyloxy)furan-2-carboxylate.

Of the compounds of formula (I), as set forth above in the Summary of the Invention, another embodiment is a compound of formula (I) wherein:
$R^1$ is —O—$R^3$—OC(O)—N($R^5$)$R^6$;
each $R^2$ is independently alkyl, haloalkyl, optionally substituted aryl, optionally substituted aralkyl, optionally substituted heterocyclyl, optionally substituted heterocyclylalkyl, optionally substituted heteroaryl or optionally substituted substituted heteroarylalkyl;
$R^3$ is an optionally substituted alkylene chain; and
$R^5$ is hydrogen, alkyl, optionally substituted cycloalkyl, optionally substituted aryl or optionally substituted aralkyl; and
$R^6$ is alkyl, optionally substituted cycloalkyl, optionally substituted aralkyl or —$R^3$—C(O)O$R^3$; and
or any $R^5$ and $R^6$, together with the nitrogen to which they are both attached, form an optionally substituted N-heterocyclyl or an optionally substituted N-heteroaryl.
Of this embodiment, one embodiment is a compound of formula (I) selected from:
1-(benzyl(methyl)carbamoyloxy)ethyl 5-(tetradecyloxy)furan-2-carboxylate;
1-((2-ethoxy-2-oxoethyl)(methyl)carbamoyloxy)ethyl 5-(tetradecyloxy)furan-2-carboxylate;
4 (2S)-2-benzyl 1-(1-(5-(tetradecyloxy)furan-2-carbonyloxy)ethyl)pyrrolidine-1,2-dicarboxylate;
1-(4-phenylcyclohexanecarbonyloxy)ethyl 5-(tetradecyloxy)furan-2-carboxylate;
1-(5-(tetradecyloxy)furan-2-carbonyloxy)ethyl 3-phenylpyrrolidine-1-carboxylate;
1-(5-(tetradecyloxy)furan-2-carbonyloxy)ethyl 3,4-dihydroisoquinoline-2(1H)-carboxylate;
1-(5-(tetradecyloxy)furan-2-carbonyloxy)ethyl piperidine-1-carboxylate;
1-(5-(tetradecyloxy)furan-2-carbonyloxy)ethyl morpholine-4-carboxylate;
1-tert-butyl 4-(1-(5-(tetradecyloxy)furan-2-carbonyloxy)ethyl)piperazine-1,4-dicarboxylate; and
1-(dicyclohexylcarbamoyloxy)ethyl 5-(tetradecyloxy)furan-2-carboxylate.

Of the compounds of formula (I), as set forth above in the Summary of the Invention, another embodiment is a compound of formula (I) wherein:
$R^1$ is —O—$R^3$—N($R^5$)$R^6$;
$R^3$ is an optionally substituted alkylene chain; and
$R^5$ is hydrogen, alkyl, optionally substituted cycloalkyl, optionally substituted aryl or optionally substituted aralkyl; and
$R^6$ is alkyl, optionally substituted cycloalkyl, optionally substituted aralkyl or —$R^3$—C(O)O$R^4$; and
or any $R^5$ and $R^6$, together with the nitrogen to which they are both attached, form an optionally substituted N-heterocyclyl or an optionally substituted N-heteroaryl.
Of this embodiment, one embodiment is a compound of formula (I) selected from:
2-(dimethylamino)ethyl 5-(tetradecyloxy)furan-2-carboxylate;
2-morpholinoethyl 5-(tetradecyloxy)furan-2-carboxylate; or
3-morpholinopropyl 5-(tetradecyloxy)furan-2-carboxylate.

Of the compounds of formula (I), as set forth above in the Summary of the Invention, another embodiment is a compound of formula (I) wherein:
$R^1$ is —O—$R^3$—N($R^4$)C(O)O$R^5$
$R^3$ is an optionally substituted alkylene chain; and
$R^4$ is optionally substituted alkyl, optionally substituted aryl, optionally substituted aralkyl, optionally substituted heteroaryl or optionally substituted heteroarylalkyl; and
$R^5$ is hydrogen, alkyl, optionally substituted cycloalkyl, optionally substituted aryl or optionally substituted aralkyl.

Of the compounds of formula (I), as set forth above in the Summary of the Invention, another embodiment is a compound of formula (I) wherein:
$R^1$ is —O—$R^3$—C(O)O$R^5$
$R^3$ is an optionally substituted alkylene chain; and
$R^5$ is hydrogen, alkyl, optionally substituted cycloalkyl, optionally substituted aryl or optionally substituted aralkyl.

Of the compounds of formula (I), as set forth above in the Summary of the Invention, another embodiment is a compound of formula (I) wherein:
$R^1$ is —O—$R^3$—C(O)N($R^5$)$R^6$;
$R^3$ is an optionally substituted alkylene chain; and
$R^5$ is hydrogen, alkyl, optionally substituted cycloalkyl, optionally substituted aryl or optionally substituted aralkyl; and
$R^6$ is alkyl, optionally substituted cycloalkyl, optionally substituted aralkyl or —$R^3$—C(O)O$R^4$;
or $R^5$ and $R^6$, together with the nitrogen to which they are both attached, form an optionally substituted N-heterocyclyl or an optionally substituted N-heteroaryl.

Of this embodiment, one embodiment is a compound of formula (I) selected from:
2-(benzyl(methyl)amino)-2-oxoethyl 5-(tetradecyloxy)furan-2-carboxylate;
tert-butyl 4-(2-(5-tetradecyloxy)furan-2-carbonyloxy)acetyl)piperazine-1-carboxylate;
2-(dicyclohexylamino)-2-oxoethyl 5-(tetradecyloxy)furan-2-carboxylate;
2-(4-cyclohexylpiperazin-1-yl)-2-oxoethyl 5-(tetradecyloxy)furan-2-carboxylate;
2-oxo-2-(4-phenylpiperzin-1-yl)ethyl-5-(tetradecyloxy)furan-2-carboxylate;
2-((2-ethoxy-2-oxoethyl)(methyl)amino)-2-oxoethyl 5-tetradecyloxy)furan-2-carboxylate;
2-oxo-2-(piperidin-1-yl)ethyl-5-(tetradecyloxy)furan-2-carboxylate;
2-morpholino-2-oxoethyl 5-(tetradecyloxy)furan-2-carboxylate;
2-(3,4-dihydroisoquinolin-2(1H)-yl)-2-oxoethyl 5-(tetradecyloxy)furan-2-carboxylate; and
(S)-benzyl 1-(2-(5-(tetradecyloxy)furan-2-carbonyloxy)acetyl)pyrrolidine-2-carboxylate.

Of the compounds of formula (I), as set forth above in the Summary of the Invention, another embodiment is a compound of formula (I) wherein:
$R^1$ is —N($R^5$)S(O)$_2$—$R^4$;
$R^4$ is optionally substituted alkyl, optionally substituted aryl, optionally substituted aralkyl, optionally substituted heteroaryl or optionally substituted heteroarylalkyl; and
$R^5$ is independently hydrogen, alkyl, optionally substituted cycloalkyl, optionally substituted aryl or optionally substituted aralkyl.

Of this embodiment, one embodiment is a compound of formula (I) which is 5-(tetradecyloxy)-N-tosylfuran-2-carboxamide.

Of the pharmaceutical compositions, as set forth above in the Summary of the Invention, one embodiment is wherein the pharmaceutical composition is a dermatological composition comprising a dermatologically effective amount of a compound of formula (I), or a pharmaceutically acceptable salt thereof, and a dermatologically acceptable excipient.

Another embodiment is wherein the dermatological composition is a gel formulation, an alcoholic gel formulation, a hydroalcoholic gel formulation, or a cream formulation.

Another embodiment is wherein the pharmaceutical composition is an oral composition comprising a dermatologically effective amount of a compound of formula (I), or a pharmaceutically acceptable salt, and a pharmaceutically acceptable excipient.

Of the method of treating a human having a dermatological disorder or condition characterized by sebaceous gland hyperactivity, as set forth above in the Summary of the Invention, one embodiment of this method is wherein the dermatological disorder or condition is selected from the group consisting of acne vulgaris, acne conglobata, choracne, rosacea, Rhinophyma-type rosacea, seborrhea, seborrheic dermatitis, sebaceous gland hyperplasia, Meibomian gland dysfunction of facial rosacea, mitogenic alopecia, and oily skin.

Another embodiment of this method is wherein the dermatological disorder is acne.

Another embodiment of this method is wherein the dermatological disorder is oily skin.

Another embodiment of this method is wherein the therapeutically effective amount of a compound of formula (I), or a pharmaceutically acceptable salt thereof, is administered topically.

Another embodiment of this method is wherein the therapeutically effective amount of a compound of formula (I), or a pharmaceutically acceptable salt thereof, is administered systemically.

Another embodiment of this method is wherein the therapeutically effective amount of a compound of formula (I), or a pharmaceutically acceptable salt thereof, is administered orally.

Of the method of treating a human having a dermatological disorder or condition characterized by sebaceous gland hyperactivity, as set forth above in the Summary of the Invention, one embodiment of this method is wherein the dermatological disorder or condition is selected from the group consisting of acne vulgaris, acne conglobata, choracne, rosacea, Rhinophyma-type rosacea, seborrhea, seborrheic dermatitis, sebaceous gland hyperplasia, Meibomian gland dysfunction of facial rosacea, mitogenic alopecia, and oily skin.

Another embodiment of this method is wherein the dermatological disorder is acne.

Another embodiment is of this method wherein the dermatological condition is oily skin.

Another embodiment of this method is wherein the therapeutically effective amount of a compound of formula (I), or a pharmaceutically acceptable salt thereof, is administered topically.

Another embodiment of this method is wherein the therapeutically effective amount of a compound of formula (I), or a pharmaceutically acceptable salt thereof, is administered systemically.

Another embodiment of this method is wherein the therapeutically effective amount of a compound of formula (I), as set forth above, or a pharmaceutically acceptable salt thereof, is administered orally.

Another embodiment of this method is wherein the pharmaceutical composition is a dermatological composition and the pharmaceutically acceptable excipient is a dermatologically acceptable excipient.

Another embodiment of this method is wherein the pharmaceutical composition is a systemic composition.

Another embodiment of this method is wherein the pharmaceutical composition is an oral composition.

Of the method of inhibiting sebaceous gland activity in a human, wherein the method comprises administering to the human in need thereof a therapeutically effective amount of a compound of formula (I), or a pharmaceutically acceptable salt thereof, as set forth above in the Summary of the Invention, one embodiment of this method is wherein the therapeutically effective amount is administered topically.

Another embodiment of this method is wherein the therapeutically effective amount is administered systemically.

Another embodiment of this method is wherein the therapeutically effective amount is administered orally.

Of the method of inhibiting sebaceous gland activity in a human, wherein the method comprises administering to the human in need thereof a pharmaceutical composition comprising a therapeutically effective amount of a compound of formula (I), or a pharmaceutically acceptable salt thereof, and a pharmaceutically acceptable excipient, as set forth above in the Summary of the Invention, one embodiment of this method is wherein the therapeutically effective amount of a compound of formula (I), as set forth above, or a pharmaceutically acceptable salt thereof, is administered topically.

Another embodiment of this method is wherein the pharmaceutical composition is administered systemically.

Another embodiment of this method is wherein the pharmaceutical composition is administered orally.

Another embodiment of this method is wherein the pharmaceutical composition is a dermatological composition and the pharmaceutically acceptable excipient is a dermatologically acceptable excipient.

Another embodiment of this method is wherein the pharmaceutical composition is a systemic composition.

Another embodiment of this method is wherein the pharmaceutical composition is an oral composition.

Of the method of treating a human having a disorder or condition characterized by inflammation, as set forth above in the Summary of the Invention, one embodiment of this method is wherein the disorder or condition is inflammatory acne.

Another embodiment of this method is wherein the therapeutically effective amount of a compound of formula (I), or a pharmaceutically acceptable salt thereof, is administered topically.

Another embodiment of this method is wherein the therapeutically effective amount of a compound of formula (I), or a pharmaceutically acceptable salt thereof, is administered systemically.

Another embodiment of this method is wherein the therapeutically effective amount of a compound of formula (I), or a pharmaceutically acceptable salt thereof, is administered orally.

Another embodiment of this method is wherein the pharmaceutical composition is a dermatological composition and the pharmaceutically acceptable excipient is a dermatologically acceptable excipient.

Another embodiment of this method is wherein the pharmaceutical composition is a systemic composition.

Another embodiment of this method is wherein the pharmaceutical composition is an oral composition.

Of the method of reducing T cell proliferation and cytokine secretion in a human having a disorder or condition characterized by inflammation, as set forth above in the Summary of the Invention, one embodiment of this method is wherein the disorder or condition is inflammatory acne.

Another embodiment of this method is wherein the therapeutically effective amount of a compound of formula (I), or a pharmaceutically acceptable salt thereof, is administered topically.

Another embodiment of this method is wherein the therapeutically effective amount of a compound of formula (I), or a pharmaceutically acceptable salt thereof, is administered systemically.

Another embodiment of this method is wherein the therapeutically effective amount of a compound of formula (I), or a pharmaceutically acceptable salt thereof, is administered orally.

Another embodiment of this method is wherein the pharmaceutical composition is a dermatological composition and the pharmaceutically acceptable excipient is a dermatologically acceptable excipient.

Another embodiment of this method is wherein the pharmaceutical composition is a systemic composition.

Another embodiment of this method is wherein the pharmaceutical composition is an oral composition.

Utility of the Invention

Increased sebum production due to sebaceous gland hyperactivity is one of several factors generally believed to be contributors to acne pathogenesis. In the formation of sebum, there is stepwise differentiation of sebocytes, a specialized epithelial cell type, arising from basal progenitor cells leading to lipid-forming cells which as they progress toward the gland outlet. These enlarged cells ultimately rupture (holocrine secretion) releasing their lipid-rich content (sebum). The overall makeup of sebum consists of squalene (12%), cholesterol (2%), wax esters (26%), and diglycerides/triglycerides/free fatty acids (57%) (see, Zouboulis et al., "An oral 5-lipoxygenase inhibitor, directly reduces sebum production". *Dermatology*. (2005) 210:36-38). Free fatty acid levels may be increased by bacterial degradation of the di- and triglycerides present within sebum (see, Thiboutot D. "Regulation of human sebaceous glands" *J. Invest Dermatol*. (2004) 123: 1-12).

Free fatty acids may also promote the inflammatory aspects of acne by activating local immune cells and their release of a variety of pro-inflammatory factors.

Fatty acid synthesis starts with the carboxylation of acetyl CoA to malonyl CoA. This irreversible reaction is the committed step in fatty acid synthesis. The synthesis of malonyl CoA is catalyzed by acetyl CoA carboxylase (ACC) (See, Brownsey, R. W. et al., "Regulation of acetyl-CoA carboxylase", *Biochem Soc. Trans*. (2006) 34: 223-227). ACC exists as two tissue-specific isoforms, a single-chain 265 kDa protein (ACC1), and a 280 kDa protein (ACC2) (See, Waldrop, G. L. et al., "Targeting acetyl-CoA carboxylase for anti-obesity therapy," *Curr. Med. Chem.—Immun., Endoc. & Metab. Agents* (2002) 3: 229-234).

In mammalian cells, ACC1 is present within the cytosol while ACC2 localizes to mitochondria. Generally, ACC1 is responsible for long-chain fatty acid synthesis while mitochondrial ACC2 acts to inhibit fatty acid oxidation. Expression of the ACC isoforms is tissue-specific and responsive to hormones and nutritional status. ACC1 is expressed at high levels in lipogenic tissues, notably in adipose, liver, and lactating mammary gland. ACC2 is a minor component of hepatic ACC and is the predominant isoform expressed, albeit at relatively low levels, in heart and skeletal muscle. Active ACC has been shown to be present in human sebaceous glands, although the ACC isoform expression pattern has not yet been described (see, Smythe, C. D. et al., "The activity of HMG-CoA reductase and acetyl-CoA carboxylase in human apocrine sweat glands, sebaceous glands, and hair follicles is regulated by phosphorylation and by exogenous cholesterol," *J. Invest. Dermatol*. (1998) 111:139-148). ACC and other fatty acid and cholesterol synthesis-regulating enzymes have been shown to be positively regulated by androgen, a key factor contributing to the increased sebum production at puberty as well as the expression of acne (see, Rosignoli, C.

et al., "Involvement of the SREBP pathway in the mode of action of androgens in sebaceous glands in vivo", *Exp. Dermatol.* (2003) 12:480-489).

ACC also catalyzes the first committed and regulated step in fatty acid synthesis in bacteria. Since membrane lipid biogenesis is essential for bacterial growth, inhibition of ACC activity may potentially decrease the growth of bacteria normally present within a comedone.

Long-chain (16-20 carbons) fatty acid acyl-CoA thioesters have been found to be potent physiological end-product inhibitors of mammalian ACC.

TOFA (5-(tetradecyloxy)-2-furancarboxylic acid) is a known hypolipidemic compound having the following structure:

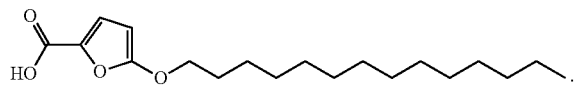 [SMILES: CCCCCCCCCCCCCCOc1ccc(C(=O)O)o1]

TOFA and pharmaceutically acceptable salts thereof are described and claimed in U.S. Pat. No. 4,110,351 (the disclosure of which is incorporated in full by reference). TOFA has been shown to reduce plasma triglyceride levels in both rats and monkeys (see, e.g., Parker, R. A. et al., *J. Med. Chem.* (1977), Vol. 20, pp. 781-791) and to inhibit hepatic fatty acid synthesis (see, e.g., Ribereau-Gayon, G., *FEBS Lett.* (1976), Vol. 62, No. 309-312; Panek, E. et al., *Lipids* (1977), Vol. 12, pp. 814-818; Kariya, T. et al., *Biochem. Biophys. Res. Commun.* (1978), Vol. 80, pp. 1022-1024; and Harris, R. A. et al., *Hormones and Energy Metabolism* (Klachko, D. M. et al., eds.), Vol. III, pp. 17-42.

TOFA, when converted intracellularly to its acyl-CoA thioester, inhibits ACC activity with a mechanism similar to long chain fatty acyl-CoA's, the physiological end-product inhibitors of ACC (see, McCune, S. A. et al., *J. Biol. Chem.* (1979), Vol. 254, No. 20, pp. 10095-10101. As a fatty acid mimetic, TOFA may exert multiple effects in sebaceous gland disorders by lowering sebum production and potentially affecting the growth of pathogenic bacteria at the treatment site.

Methods of using TOFA to inhibit sebaceous gland hyperactivity and in the treatment of acne and inflammation are known. See, for example, PCT Published Patent Application No. WO 2008/058034.

Analogs of TOFA, such as the compounds of the invention, are disclosed herein as effective inhibitors of sebaceous gland activity, and are therefore useful in treating a mammal, preferably a human, having a dermatological disorder or condition characterized by sebaceous gland hyperactivity, such as acne. The analogs of TOFA disclosed herein may also be useful in treating a mammal having a disorder or condition characterized by inflammation by reducing T cell proliferation and cytokine secretion.

Preparation of the Compounds of the Invention

The following Reaction Schemes represent methods of preparing the compounds of the invention, i.e., compounds of formula (I):

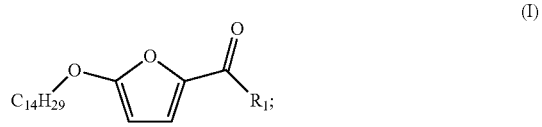

wherein $R^1$ is as defined above in the Summary of the Invention, as a stereoisomer or as a mixture thereof, or a pharmaceutically acceptable salt thereof.

It is understood that in the following description, combinations of substituents and/or variables of the depicted formulae are permissible only if such contributions result in stable compounds.

It will also be appreciated by those skilled in the art that in the process described below the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (e.g., t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R" (where R" is alkyl, aryl or aralkyl), p-methoxybenzyl, trityl and the like. Suitable protecting groups for carboxylic acid include alkyl, aryl or arylalkyl esters.

Protecting groups may be added or removed in accordance with standard techniques, which are known to one skilled in the art and as described herein.

The use of protecting groups is described in detail in Greene, T. W. and P. G. M. Wuts, *Protective Groups in Organic Synthesis* (2006), 4$^{th}$ Ed., Wiley. The protecting group may also be a polymer resin such as a Wang resin or a 2-chlorotrityl-chloride resin.

It is understood that one skilled in the art would be able to make the compounds of the invention by methods similar to the ones described below in the Reaction Schemes or by methods known to one skilled in the art. It is also understood that one skilled in the art would be able to make in a similar manner as described below other compounds of the invention not specifically illustrated below by using the appropriate starting components and modifying the parameters of the synthesis as needed. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, e.g., Smith, M. B. and J. March, *Advanced Organic Chemistry: Reactions*, Mechanisms, and Structure, 5th edition (Wiley, December 2000)) or prepared as described herein. TOFA is commercially available, for example, from Cedarlane Laboratories, Inc.

REACTION SCHEME 1

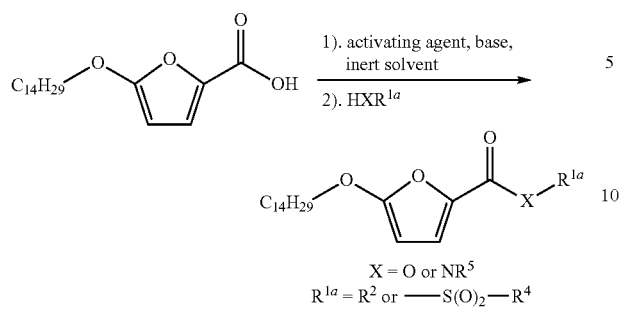

X = O or NR⁵
R¹ᵃ = R² or —S(O)₂—R⁴

The compounds of the present invention can be prepared as in Reaction Scheme 1, where $R^2$, $R^4$ and $R^5$ are each as described above in the Summary of the Invention, by activating the carboxylic group of 5-(tetradecyloxy)furan-2-carboxylic acid (TOFA) with a suitable reagent including but not limited to: oxalyl chloride, thionyl chloride, acetic anhydride, trifluoroacetic anhydride, toluenesulfonyl chloride, hydroxysuccinamide, hydroxybenzotriazole, dicyclohexylcarbodiimide, or carbonyldiimidazole. The activated acid compound is generally prepared at temperatures of between 0° C. and ambient and may be isolated or may be reacted in situ with a suitable alcohol or sulfonamide in the presence of a base (triethylamine, pyridine, etc.). The product from the reaction can be isolated and purified employing standard techniques such as solvent extraction, chromatography, crystallization, distillation, and the like.

REACTION SCHEME 2

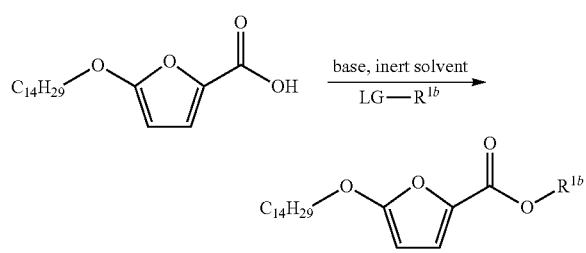

LG = leaving group
R¹ᵇ = R², —R³—OC(O)N(R⁵)R⁶ or —R³—C(O)N(R⁵)R⁶

The compounds of the present invention can also be prepared as outlined in Reaction Scheme 2 where each $R^2$, $R^3$, $R^5$ and $R^6$ are as described above in the Summary of the Invention. TOFA can be reacted with an alkylating agent (either purchased commercially or prepared using techniques well known in the art) having a suitable leaving group (halide, triflate, tosylate, mesylate, and the like) in the presence of a suitable base (including but not limited to potassium carbonate, cesium carbonate, tetrabutylammonium hydroxide, triethylamine, etc.). The reactions can be carried out in a suitable solvent such as N,N-dimethylformamide and are usually performed at a temperature between ambient and 70° C. The product from the reaction can be isolated and purified employing standard techniques such as solvent extraction, chromatography, crystallization, distillation, and the like.

REACTION SCHEME 3

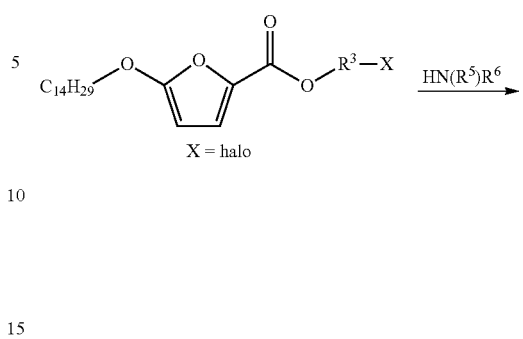

X = halo

The compounds of the present invention can also be prepared as shown above in Reaction Scheme 3. TOFA can be reacted with a linker containing two suitable leaving groups (halide, triflate, tosylate, mesylate, and the like). The initial reaction is performed as in Reaction Scheme 2 above. The product of this reaction is then reacted with a suitable nucleophile including but not limited to amines (shown above), alcohols or phenols in a suitable solvent such as DMF or THF. The reaction is generally performed at ambient temperature for 12 hrs in the presence of a suitable base which may be tetrabutylammonium hydroxide, excess of the amine nucleophile, triethylamine, or the like. The product from the reaction can be isolated and purified employing standard techniques such as solvent extraction, chromatography, crystallization, distillation, and the like.

In some cases the final product of the Reaction Schemes shown above may be further modified, for example by manipulation of substituents. These manipulations may include, but are not limited to, oxidation, reduction, alkylation, acylation and hydrolysis, as needed to prepare the compounds of the invention. Such manipulations are within the knowledge of one skilled in the organic chemistry field. These manipulations may also include the removal of a protecting group such as a Boc group, a tetrahydropyran group or the like by methods outlined in T. W. Greene and P. G. M. Wuts, "Protective Groups in Organic Synthesis", Second Edition, John Wiley and Sons, New York, 1991.

All compounds of the invention as prepared above and below which exist in free base or acid form may be converted to their pharmaceutically acceptable salt by treatment with the appropriate inorganic or organic base or acid by methods known to one skilled in the art. Salts of the compounds prepared herein may be converted to their free base or acid by standard techniques known to one skilled in the art.

The following Synthetic Examples, which are directed to the preparation of the compounds of formula (I), are provided as a guide to assist in the practice of the invention, and are not intended as a limitation on the scope of the invention. Mass spectrometer samples were analyzed on a MicroMass mass spectrometer operated in single MS mode with electrospray ionization. Samples were introduced into the mass spectrometer using chromatography. 1H NMR spectra were recorded at 400 MHz using a Bruker instrument or at 300 MHz using a Varian instrument. Elemental analysis was performed by Canadian Microanalytical Ltd., Delta, BC, Canada.

SYNTHETIC EXAMPLE 1

Synthesis of 2,2,2-trifluoroethyl 5-(tetradecyloxy)furan-2-carboxylate

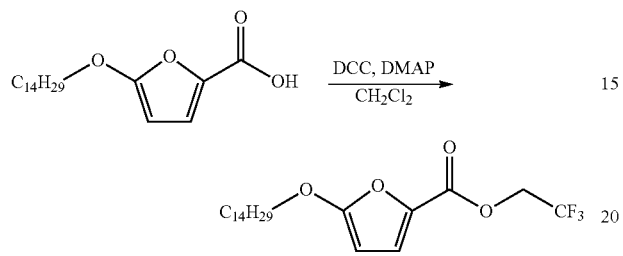

To a stirred, room temperature suspension of 5-(tetradecyloxy)furan-2-carboxylic acid (1.3 g, 4.0 mmol) in $CH_2Cl_2$ (40 mL) was added N,N'-dicyclohexylcarbodiimide (0.990 g, 4.8 mmol), N,N-dimethylaminopyridine (0.488 g, 4.0 mmol) and 2,2,2-trifluoroethanol (0.875 mL, 12.0 mmol). The flask was capped and stirring was continued for 16 hrs at which time TLC (10% EtOAc in Hexanes $R_f$=0.05 (SM) and 0.25 (Prod)) indicated complete consumption of the starting material. The resulting suspension was diluted with $CH_2Cl_2$ (40 mL), filtered and concentrated. This crude material was purified by flash chromatography eluting with 5-20% EtOAc in Hexanes. The resulting solid was further purified by recrystallization in 30 mL of hot 2-propanol with the addition of a minimum amount of water to yield 1.13 g (70%) of the title compound as white needles. MS (m/z, ES−): 406.0 (M−1, 100%); EA found for $C_{23}H_{36}F_3NO_2$: C, 62.20; H, 8.18; calcd: C, 62.05; H, 8.18; $^1$H NMR (400 MHz, DMSO-$d_6$) δ: 7.4 (d, 1H), 5.7 (d, 1H), 4.9 (q, 2H), 4.2 (t, 2H), 1.50-1.57 (m, 2H), 1.10-1.20 (m, 22H), 0.85 (t, 3H).

SYNTHETIC EXAMPLE 2

Synthesis of 2,2,2-trichloroethyl 5-(tetradecyloxy)furan-2-carboxylate

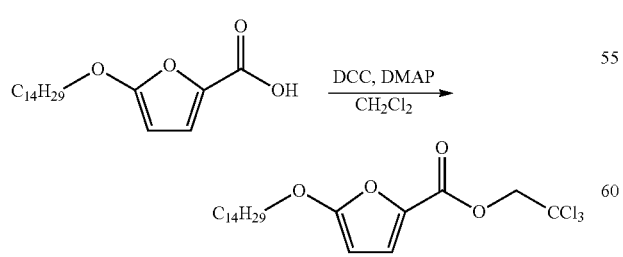

The title compound was prepared as described in Example 1 starting from 0.228 g (0.7 mmol) of 5-(tetradecyloxy)furan-2-carboxylic acid and 0.196 mL (2.04 mmol) of 2,2,2-trichloroethanol. $^1$H NMR (400 MHz, DMSO-$d_6$) δ: 7.4 (d, 1H), 5.74 (d, 1H), 5.03 (s, 2H), 4.19 (t, 2H), 1.7 (p, 2H), 1.2-1.5 (m, 22H), 0.85 (t, 3H).

SYNTHETIC EXAMPLE 3

Synthesis of isopropyl 5-(tetradecyloxy)furan-2-carboxylate

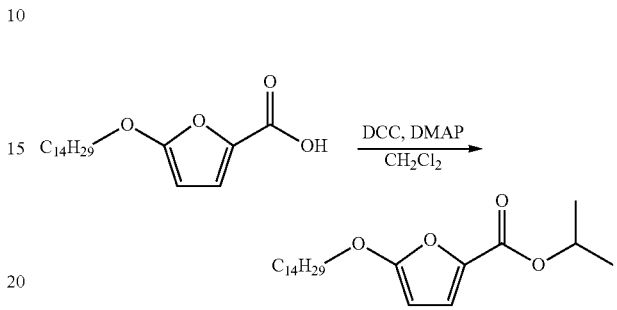

The title compound was prepared as described in Example 1 starting from 0.228 g (0.7 mmol) of 5-(tetradecyloxy)furan-2-carboxylic acid and 0.161 mL (2.1 mmol) of 2-propanol. MS (m/z, ES+): 366.30 (M+, 100%); $^1$H NMR (400 MHz, DMSO-$d_6$) δ: 7.2 (d, 1H), 5.6 (d, 1H), 5.0 (p, 1H), 4.1 (t, 2H), 1.7 (p, 2H), 1.3-1.4 (m, 2H), 1.23 (d, 6H), 1.2 (s, 20H), 0.85 (t, 3H).

SYNTHETIC EXAMPLE 4

Synthesis of methyl 5-(tetradecyloxy)furan-2-carboxylate

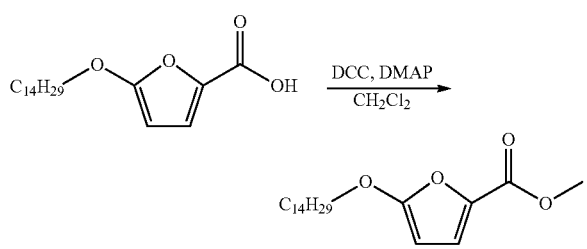

The title compound was prepared as described in Example 1 starting from 0.228 g (0.7 mmol) of 5-(tetradecyloxy)furan-2-carboxylic acid and 0.083 mL (2.1 mmol) of methanol. MS (m/z, ES+): 339.34 (M+1, 100%).

SYNTHETIC EXAMPLE 5

Synthesis of 2-bromoethyl 5-(tetradecyloxy)furan-2-carboxylate

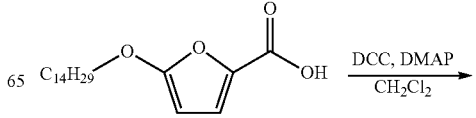

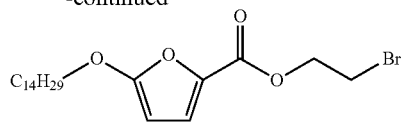

The title compound was prepared as described in Example 1 starting from 0.228 g (0.7 mmol) of 5-(tetradecyloxy)furan-2-carboxylic acid and 0.150 mL (2.1 mmol) of 2-bromoethanol. MS (m/z, ES+): 446.30 ($^{79}$BrM+1, 100%), 448.30 ($^{81}$BrM+1, 80%); $^1$H NMR (400 MHz, DMSO-d$_6$) δ: 7.30 (d, 1H), 5.67 (d, 1H), 4.49 (t, 2H), 4.16 (t, 2H), 3.73 (t, 2H), 1.72 (p, 2H), 1.3-1.45 (m, 2H), 1.25 (s, 20H), 0.85 (t, 3H); EA found for C$_{21}$H$_{35}$BrO$_4$: C, 58.93: H, 8.52; calcd: C, 58.47; H, 8.18.

SYNTHETIC EXAMPLE 6

Synthesis of 5-(tetradecyloxy)-N-tosylfuran-2-carboxamide

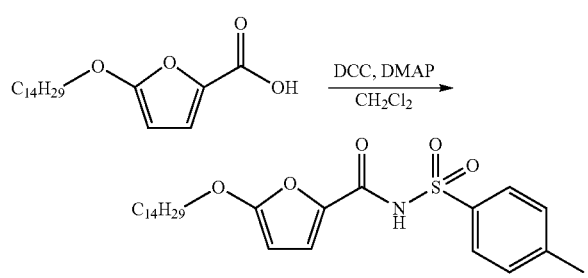

The title compound was prepared as described in Example 1 starting from 0.228 g (0.7 mmol) of 5-(tetradecyloxy)furan-2-carboxylic acid and 0.361 g (2.1 mmol) of 4-methylbenzenesulfonamide. MS (m/z, ES–): 476.63 (M–1, 100%).

SYNTHETIC EXAMPLE 7

Synthesis of (5-methyl-2-oxo-1,3-dioxol-4-yl)methyl 5-(tetradecyloxy)furan-2-carboxylate

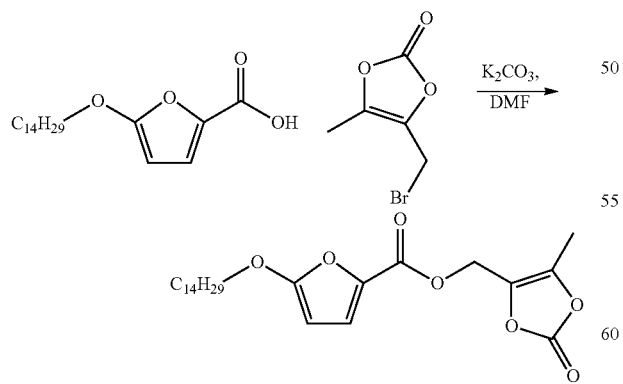

To a stirred, room temperature solution of 5-(tetradecyloxy)furan-2-carboxylic acid (0.228 g, 0.70 mmol) in DMF (4 mL) was added potassium carbonate (0.146 g, 1.05 mmol) and 4-(bromomethyl)-5-methyl-1,3-dioxol-2-one (0.160 g, 0.84 mmol). The reaction vessel was capped and stirring was continued for 14 hrs at which time TLC ((20% EtOAc in Hexanes R$_f$=0.10 (SM) and 0.40 (Prod)) indicated complete consumption of the starting material. The reaction was quenched by the addition of water (5 mL), brine (5 mL) and EtOAc (30 mL). The biphasic mixture was transferred to a separatory funnel and the organic phase was extracted 3 times with brine (3×10 mL). The organic phase was dried and concentrated to give a colourless oil. The resulting crude material was purified by flash chromatography eluting with 5-20% EtOAc in hexanes to yield a colourless syrup that solidified on standing. $^1$H NMR (400 MHz, DMSO-d$_6$) δ: 7.2 (d, 1H), 5.6 (d, 1H), 5.1 (s, 2H), 4.1 (t, 2H), 2.18 (s, 3H), 1.6-1.8 (m, 2H), 1.3-1.4 (m, 2H), 1.23 (d, 6H), 1.2 (s, 20H), 0.85 (t, 3H).

SYNTHETIC EXAMPLE 8

Synthesis of 1-(benzyl(methyl)carbamoyloxy)ethyl 5-(tetradecyloxy)furan-2-carboxylate

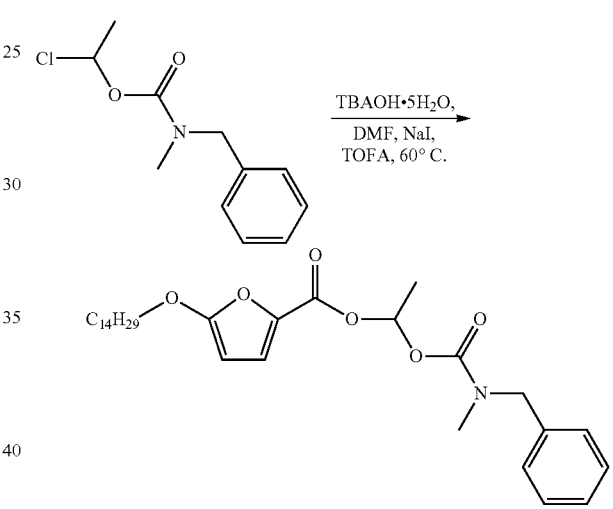

A. 1-chloroethyl benzyl(methyl)carbamate

To a vigorously stirred suspension of N-methylbenzylamine (0.260 mL, 2 mmol) in EtOAc (3 mL) and 3 mL of saturated NaHCO$_3$ solution was added 1-chloroethyl chloroformate (0.160 mL, 2 mmol). Effervescence was observed. Once gas production had ceased, the reaction mixture was diluted with hexanes (10 mL). The aqueous phase was removed and the organic phase was washed with brine (5 mL), dried and concentrated to give the crude product as an oil (~0.250 g). The compound was used in the subsequent step without further purification.

B. 1-(benzyl(methyl)carbamoyloxy)ethyl 5-(tetradecyloxy)furan-2-carboxylate

The above prepared 1-chloroethyl benzyl(methyl)carbamate was dissolved in N,N-dimethylformamide (5 mL) and then 5-(tetradecyloxy)furan-2-carboxylic acid (0.180 g, 0.544 mmol), tetrabutylammonium hydroxide pentahydrate (0.209 g, 0.60 mmol), and sodium iodide (~15 mg) were added to the reaction vessel. The resulting suspension was heated to 60° C. with stirring for 14 hrs. HPLC analysis of the reaction solution indicated that all of the starting material had been converted to a product of lower polarity. The reaction was then quenched with brine (5 mL), water (5 mL) and EtOAc (70 mL). The organic phase was washed successively with water (30 mL) and brine (30 mL) and then dried and concentrated. The resulting crude material was purified by flash chromatography eluting with EtOAc in hexanes, 5-20% to yield 0.120 g (43%) of the title compound as a slightly brown oil. $^1$H NMR (300 MHz, CDCl$_3$) δ: 7.15-7.40 (m, 6H), 7.05 (p, 1H), 5.30 (d, 1H), 4.40-4.60 (m, 2H), 4.10 (t, 2H), 2.85 (d, 3H) 1.7-1.9 (m, 2H), 1.79 (p, 2H), 1.55-1.62 (m, 3H), 1.18-1.50 (m, 22H), 0.89 (t, 3H).

SYNTHETIC EXAMPLE 9

Synthesis of 1-((2-ethoxy-2-oxoethyl)(methyl)carbamoyloxy)ethyl 5-(tetradecyloxy)furan-2-carboxylate

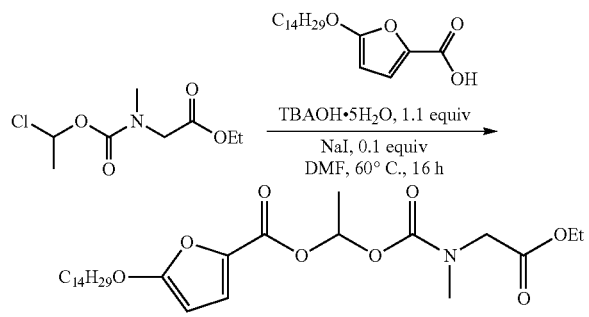

The title compound was prepared as in Example 8, Steps 1 and 2 starting with 0.20 mL (1.8 mmol) of 1-chloroethylchloroformate, 0.267 g (1.8 mmol) of sarcosine ethyl ester hydrochloride and 4 mL of saturated NaHCO$_3$ solution. $^1$H NMR (300 MHz, CDCl$_3$) δ: 7.18 (t, 1H), 6.98 (dq, 1H), 5.3 (d, 1H), 4.03-4.23 (m, 5H), 3.8-3.9 (m, 1H), 2.98 (s, 3H), 1.75 (p, 2H), 1.52-1.6 (m, 3H), 1.2-1.5 (m, 27H), 0.85 (t, 3H).

SYNTHETIC EXAMPLE 10

Synthesis of (2S)-2-benzyl 1-(1-(5-(tetradecyloxy)furan-2-carbonyloxy)ethyl)pyrrolidine-1,2-dicarboxylate

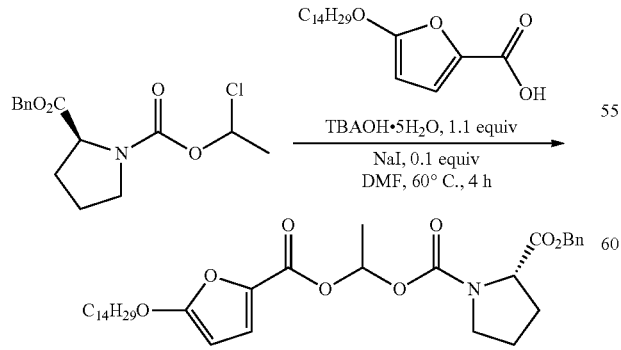

The title compound was prepared as in Example 8, Steps 1 and 2 starting with 0.20 mL (1.8 mmol) of 1-chloroethylchloroformate, 0.435 g (1.8 mmol) of L-benzylproline hydrochloride and 4 mL of saturated NaHCO$_3$ solution. The compound was isolated as a mixture of two diastereomers. $^1$H NMR (300 MHz, CDCl$_3$) δ: 7.25-7.4 (m, 5H), 6.9-7.2 (m, 2H), 5.0-5.3 (m, 2H), 4.35-4.45 (m, 1H), 4.0-4.18 (m, 2H), 3.4-3.65 (m, 2H), 2.1-2.3 (m, 1H), 1.8-2.0 (m, 2H), 1.65-1.8 (m, 2H), 1.45-1.6 (m, 3H), 1.2-1.5 (m, 24H), 0.9 (t, 3H).

SYNTHETIC EXAMPLE 11

Synthesis of 1-(4-phenylcyclohexanecarbonyloxy)ethyl 5-(tetradecyloxy)furan-2-carboxylate

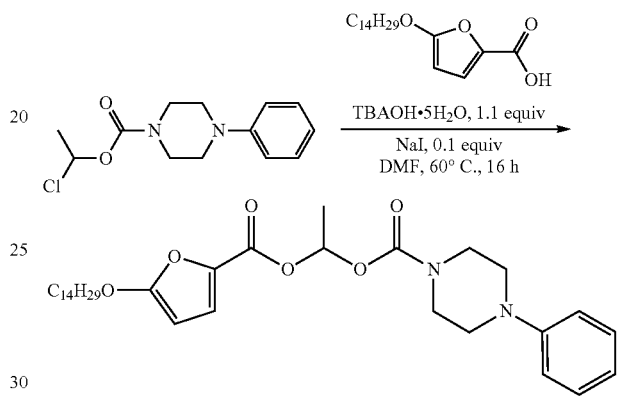

The title compound was prepared as in Example 8, Steps 1 and 2 starting with 0.20 mL (1.8 mmol) of 1-chloroethylchloroformate, 0.303 g (1.8 mmol) of 1-phenyl piperazine and 4 mL of saturated NaHCO$_3$ solution. $^1$H NMR (300 MHz, CDCl$_3$) δ: 7.25-7.35 (m, 2H), 7.20 (d, 1H, J=4 Hz), 7.04 (q, 1H, J=5 Hz), 6.85-6.95 (m, 3H), 5.30 (d, 1H, J=4 Hz), 4.15 (app t, 2H, J=3.5 Hz), 3.63 (br t, 4H), 3.18 (br s, 4H), 1.8 (p, 2H, J=8 Hz), 1.60 (d, 3H, J=6 Hz), 1.20-1.5 (m, 22H), 0.87 (t, 3H, J=7 Hz).

SYNTHETIC EXAMPLE 12

Synthesis of 1-(5-(tetradecyloxy)furan-2-carbonyloxy)ethyl 3-phenylpyrrolidine-1-carboxylate

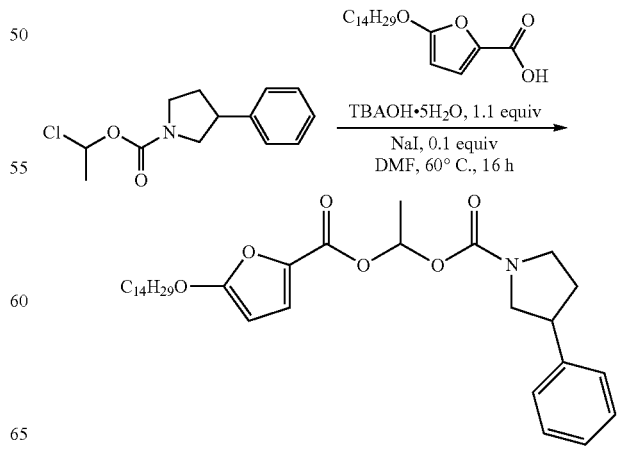

The title compound was prepared as in Example 8, Steps 1 and 2 starting with 0.20 mL (1.8 mmol) of 1-chloroethylchloroformate, 0.167 g (1.8 mmol) of 3-phenyl pyrrolidine and 4 mL of saturated NaHCO₃ solution. The compound was isolated as a mixture of four diastereomers. ¹H NMR (300 MHz, CDCl₃) δ: 7.18-7.3 (m, 5H), 7.2 (q, 1H), 6.93 (d, 1H), 5.3 (d, 1H), 4.12 (t, 2H), 3.1-4.0 (m, 5H), 2.2-2.35 (m, 1H), 1.95-2.05 (m, 1H), 1.75 (t, 2H), 1.5-1.65 (m, 3H), 1.2-1.5 (m, 22H), 0.9 (t, 3H).

SYNTHETIC EXAMPLE 13

Synthesis of 1-(5-(tetradecyloxy)furan-2-carbonyloxy)ethyl 3,4-dihydroisoquinoline-2(1H)-carboxylate

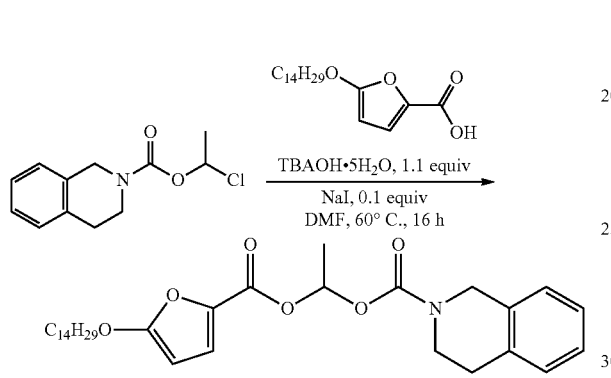

The title compound was prepared as in Example 8, Steps 1 and 2 starting with 0.20 mL (1.8 mmol) of 1-chloroethylchloroformate, 0.305 g (1.8 mmol) of 1,2,3,4-tetrahydroisoquinoline hydrochloride and 4 mL of saturated NaHCO₃ solution. ¹H NMR (300 MHz, CDCl₃) δ: 7.0-7.2 (m, 6H), 5.3 (d, 1H), 4.6 (d, 2H), 4.1 (t, 2H), 3.6-3.75 (m, 2H), 2.8-2.87 (m, 2H), 1.75 (p, 2H), 1.5-1.62 (m, 3H), 1.2-1.5 (m, 22H), 0.9 (t, 3H).

SYNTHETIC EXAMPLE 14

Synthesis of 1-(5-(tetradecyloxy)furan-2-carbonyloxy)ethyl piperidine-1-carboxylate

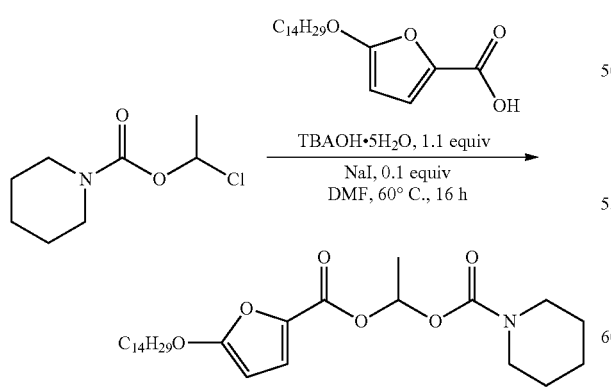

The title compound was prepared as in Example 8, Steps 1 and 2 starting with 0.20 mL (1.8 mmol) of 1-chloroethylchloroformate, 0.178 mL (1.8 mmol) of piperidine and 4 mL of saturated NaHCO₃ solution. ¹H NMR (300 MHz, CDCl₃) δ: 7.18 (d, 1H), 6.98 (q, 1H), 5.3 (d, 1H), 4.08-4.18 (m, 2H), 3.38-3.42 (m, 4H), 1.5-1.8 (m, 33H), 0.89 (t, 3H).

SYNTHETIC EXAMPLE 15

Synthesis of 1-(5-(tetradecyloxy)furan-2-carbonyloxy)ethyl morpholine-4-carboxylate

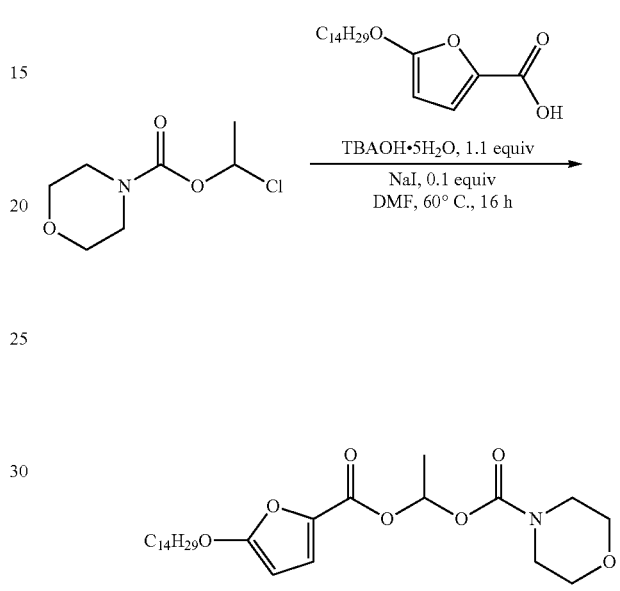

The title compound was prepared as in Example 8, Steps 1 and 2 starting with 0.20 mL (1.8 mmol) of 1-chloroethylchloroformate, 0.157 mL (1.8 mmol) of morpholine and 4 mL of saturated NaHCO₃ solution. ¹H NMR (300 MHz, CDCl₃) δ: 7.18 (d, 1H), 7.05 (q, 1H), 5.32 (d, 1H), 4.1 (t, 2H), 3.6-3.6 (m, 4H), 3.45-3.55 (m, 4H), 1.75 (p, 2H), 1.5-1.65 (m, 3H), 1.2-1.5 (m, 22H), 0.85 (t, 3H).

SYNTHETIC EXAMPLE 16

Synthesis of 1-tert-butyl 4-(1-(5-(tetradecyloxy)furan-2-carbonyloxy)ethyl)piperazine-1,4-dicarboxylate

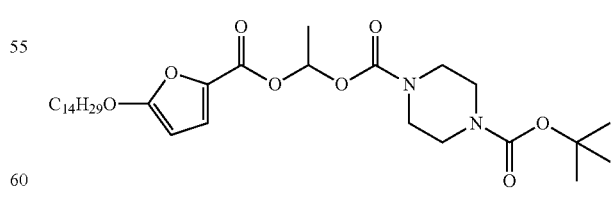

The title compound was prepared as in Example 8, Steps 1 and 2 starting with 0.20 mL (1.8 mmol) of 1-chloroethylchloroformate, 0.335 mg (1.8 mmol) of tert-butyl 1-piperazine carboxylate and 4 mL of saturated NaHCO₃ solution. ¹H NMR (300 MHz, CDCl₃) δ: 7.2 (d, 1H), 6.97 (q, 1H), 5.3 (d, 1H), 4.1 (t, 2H), 3.4 (br s, 8H), 1.75 (p, 2H), 1.5-1.6 (m, 3H) 1.5 (s, 9H), 1.2-1.5 (m, 22H), 0.9 (t, 3H).

SYNTHETIC EXAMPLE 17

Synthesis of 1-(dicyclohexylcarbamoyloxy)ethyl 5-(tetradecyloxy)furan-2-carboxylate

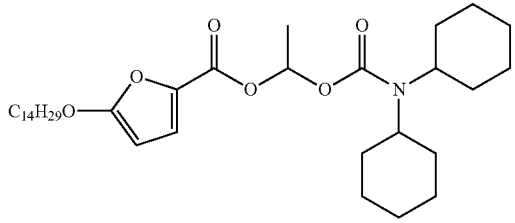

The title compound was prepared as in Example 8, Steps 1 and 2 starting with 0.20 mL (1.8 mmol) of 1-chloroethylchloroformate, 0.220 mg (1.8 mmol) of dicyclohexylamine and 3 mL of saturated NaHCO₃ solution. ¹H NMR (300 MHz, CDCl₃) δ: 7.1 (d, 1H), 7.0 (q, 1H), 5.3 (d, 1H), 4.05-4.15 (m, 2H), 3.6 (br s, 1H), 3.2 (br s, 1H), 1.65-1.8 (m, 10H), 1.55-1.65 (m, 11H), 1.2-1.5 (m, 24H), 1.0-1.2 (m, 2H), 0.8 (t, 3H).

SYNTHETIC EXAMPLE 18

Synthesis of 2-(dimethylamino)ethyl 5-(tetradecyloxy)furan-2-carboxylate

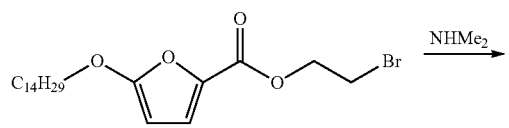

To a solution of 2-bromoethyl 5-(tetradecyloxy)furan-2-carboxylate (0.186 g, 0.43 mmol) (prepared in Example 5) in THF at 0° C. was added dimethylamine (1 mL of a 2M solution in THF, 2.15 mmol) with stirring. The solution was allowed to warm to room temperature and stirring was continued for 12 hrs at which time the reaction was concentrated to dryness. The crude material was purified by flash chromatography eluting with ethyl acetate in hexanes (5-35%) to yield 0.121 g (71%) of the title compound as a waxy, colourless solid. MS (m/z, ES+): 396.29 (M+1, 100%); ¹H NMR (400 MHz, DMSO-d₆) δ: 7.2 (d, 1H), 5.6 (d, 1H), 4.23 (t, 2H), 4.13 (t, 2H), 2.53 (t, 2H), 2.18 (s, 6H), 1.7 (p, 2H), 1.2-1.5 (m, 22H), 0.85 (t, 3H).

SYNTHETIC EXAMPLE 19

Synthesis of 3-morpholinopropyl 5-(tetradecyloxy)furan-2-carboxylate

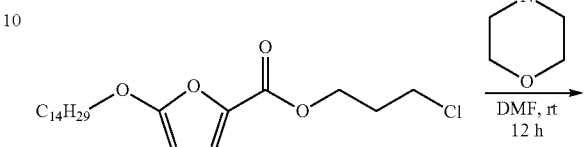

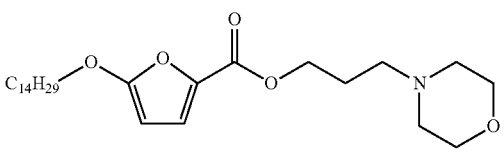

A. 3-chloropropyl 5-(tetradecyloxy)furan-2-carboxylate

To a vigorously stirred suspension of 5-(tetradecyloxy)furan-2-carboxylic acid (0.650 g, 2.0 mmol) in 10 mL of N,N-dimethylformamide was added 3-chlorobromopropane (0.618 mL, 6.0 mmol), tetrabutylammonium hydroxide pentahydrate (0.734 g, 4.2 mmol) and sodium iodide (~20 mg). The suspension appeared to go into solution briefly, and then a very finely dispersed white precipitate was observed. The reaction was allowed to stir for 12 hrs. The suspension was then diluted with EtOAc (100 mL), brine (50 mL) and water (50 mL). The phases were separated and the organic phase was washed with water (50 mL) and brine (50 mL). The organic phase was then dried and concentrated to yield 0.554 g of the title compound. This material was used in the subsequent step without further purification.

B. 3-(piperidin-1-yl)propyl 5-(tetradecyloxy)furan-2-carboxylate

To a solution of the above prepared 3-chloropropyl 5-(tetradecyloxy)furan-2-carboxylate (0.272 g, 0.68 mmol) in 6 mL of N,N-dimethylformamide was added morpholine (0.535 mL, 6.1 mmol) and sodium iodide (10 mg). The resulting solution was stirred at 55° C. for 36 hrs at which time HPLC analysis of the reaction mixture indicated near complete consumption of the starting material. The solution was diluted with EtOAc (30 mL), brine (10 mL) and water (10 mL) such that both phases were clear solutions. The phases were separated and the organic phase was washed with water (20 mL) and brine (20 mL) and then dried and concentrated. The crude material was purified by flash chromatography eluting with 5-40% EtOAc in hexanes to yield 0.217 g of the title compound. ¹H NMR (300 MHz, CDCl₃) δ: 7.10 (d, 1H), 5.30 (d, 1H), 4.30 (t, 2H), 4.10 (t, 2H), 3.7 (t, 4H), 2.40-2.50 (m, 6H), 1.90 (p, 2H), 1.76 (p, 2H), 1.18-1.50 (m, 22H), 0.89 (t, 3H).

SYNTHETIC EXAMPLE 20

Synthesis of 2-(benzyl(methyl)amino)-2-oxoethyl 5-(tetradecyloxy)furan-2-carboxylate

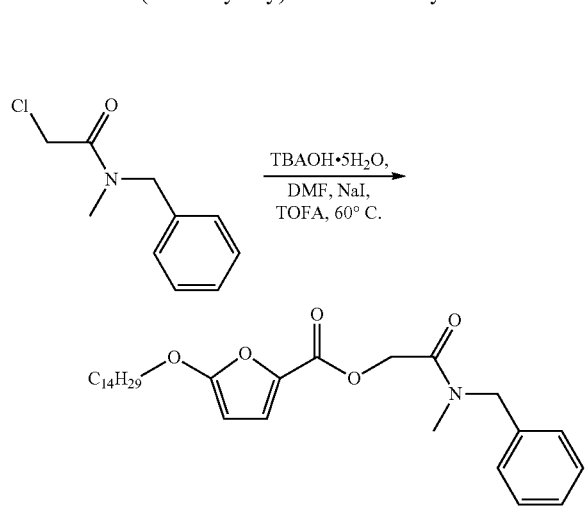

A. N-benzyl-2-chloro-N-methylacetamide

To a vigorously stirred suspension of N-methylbenzylamine (0.260 mL, 2 mmol) in EtOAc (3 mL) and 3 mL of saturated NaHCO₃ solution was added chloroacetyl chloride (0.160 mL, 2 mmol). Effervescence was observed. Once gas production had ceased, the reaction mixture was diluted with hexanes (10 mL). The phases were separated and the organic phase was washed with brine (5 mL), dried and concentrated to yield ~0.250 g of the title compound as an oil. The crude material was used in the subsequent step without further purification.

B. 2-(benzyl(methyl)amino)-2-oxoethyl 5-(tetradecyloxy)furan-2-carboxylate

The above prepared N-benzyl-2-chloro-N-methylacetamide (0.250 g) was dissolved in 10 mL of N,N-dimethylformamide. To this solution were added 5-(tetradecyloxy)furan-2-carboxylic acid (0.180 g, 0.544 mmol), tetrabutylammonium hydroxide pentahydrate (0.209 g, 0.554 mmol), and sodium iodide (~15 mg). The suspension was heated to 60° C. with stirring for 14 hrs. The reaction was quenched with brine (5 mL), water (5 mL) and EtOAc (40 mL). The phases were separated and the organic phase was further diluted with EtOAc (30 mL), washed successively with water (30 mL) and brine (30 mL) and then dried and concentrated. The resulting crude material was purified by flash chromatography eluting with 5-20% EtOAc in hexanes to give the desired compound as a viscous oil. The material was further purified by recrystallization from 2-propanol and water to yield 0.130 g (52%) of the title compound. ¹H NMR (300 MHz, CDCl₃) δ: 7.20-7.40 (m, 6H), 5.30-5.35 (m, 1H), 4.92 (s, 2H), 4.50-4.61 (app d, 2H), 4.10 (m, 2H), 2.90-2.98 (app d, 3H), 1.79 (p, 2H), 1.18-1.50 (m, 22H), 0.89 (t, 3H).

SYNTHETIC EXAMPLE 21

Synthesis of tert-butyl 4-(2-(5-tetradecyloxy)furan-2-carbonyloxy)acetyl)piperazine-1-carboxylate

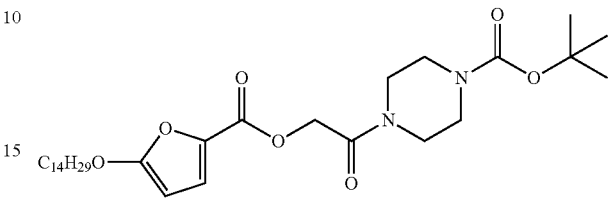

The title compound was prepared as in Example 20, Steps 1 and 2 starting with 0.373 g (2.0 mmol) of tert-butyl 1-piperazine carboxylate and 0.160 mL (2 mmol) of chloroacetyl chloride except that the reaction mixture in Step 1 was diluted in EtOAc rather than hexanes. ¹H NMR (300 MHz, CDCl₃) δ: 7.22 (d, 1H), 5.3 (d, 1H), 4.85 (s, 2H), 4.15 (t, 2H), 3.55-3.65 (m, 2H), 3.4-3.52 (m, 6H), 1.75 (p, 2H), 1.45 (s, 9H), 1.2-1.5 (m, 22H), 0.8 (t, 3H).

SYNTHETIC EXAMPLE 22

Synthesis of 2-(dicyclohexylamino)-2-oxoethyl 5-(tetradecyloxy)furan-2-carboxylate

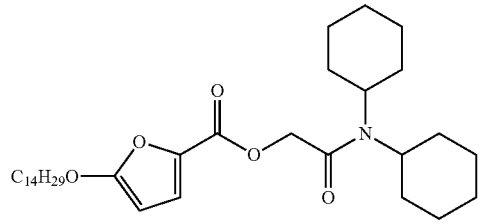

The title compound was prepared as in Example 20, Steps 1 and 2 starting with 0.244 mL (2.0 mmol) of dicyclohexylamine and 0.160 mL (2 mmol) of chloroacetyl chloride except that the reaction mixture in Step 1 was diluted in EtOAc rather than hexanes. ¹H NMR (300 MHz, CDCl₃) δ: 7.2 (d, 1H), 5.3 (d, 1H), 4.8 (s, 2H), 4.1-4.18 (m, 2H), 3.22 (t, 2H), 2.9-3.05 (m, 2H), 2.3-2.5 (m, 2H), 1.1-1.9 (m, 40H), 0.83 (t, 3H).

SYNTHETIC EXAMPLE 23

Synthesis of 2-(4-cyclohexylpiperazin-1-yl)-2-oxoethyl 5-(tetradecyloxy)furan-2-carboxylate

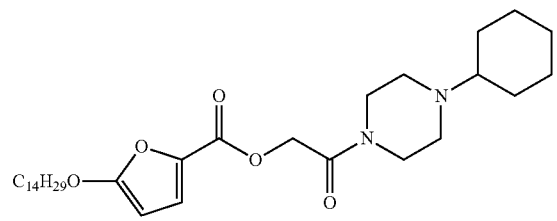

The title compound was prepared as in Example 20, Steps 1 and 2 starting with 0.337 g (2.0 mmol) of 1-cyclohexylpiperazine and 0.160 mL (2 mmol) of chloroacetyl chloride except that the reaction mixture in Step 1 was diluted in EtOAc rather than hexanes. $^1$H NMR (300 MHz, CDCl$_3$) δ: 7.22 (d, 1H), 5.3 (d, 1H), 4.9 (s, 2H), 4.1 (t, 2H), 3.6 (t, 2H), 3.4 (t, 2H), 2.57 (p, 4H), 2.2-2.35 (m, 1H), 1.5-1.8 (m, 6H), 1.2-1.5 (m, 28H), 0.83 (t, 3H).

SYNTHETIC EXAMPLE 24

Synthesis of 2-oxo-2-(4-phenylpiperzin-1-yl)ethyl-5-(tetradecyloxy)furan-2-carboxylate

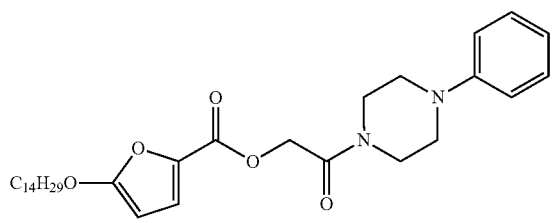

The title compound was prepared as in Example 20, Steps 1 and 2 starting with 0.324 g (2.0 mmol) of 1-phenyl piperazine and 0.160 mL (2 mmol) of chloroacetyl chloride except that the reaction mixture in Step 1 was diluted in EtOAc rather than hexanes. The title compound was further purified by recrystallization from isopropanol and water. $^1$H NMR (300 MHz, CDCl$_3$) δ: 7.23-7.35 (m, 4H), 6.9 (d, 2H), 5.34 (d, 1H), 4.95 (s, 2H), 4.13 (t, 2H), 3.78-3.82 (m, 2H), 3.69-3.63 (m, 2H), 3.15-3.25 (m, 4H), 1.75 (p, 2H), 1.2-1.5 (m, 22H), 0.86 (t, 3H).

SYNTHETIC EXAMPLE 25

Synthesis of 2-((2-ethoxy-2-oxoethyl)(methyl)amino)-2-oxoethyl 5-tetradecyloxy)furan-2-carboxylate

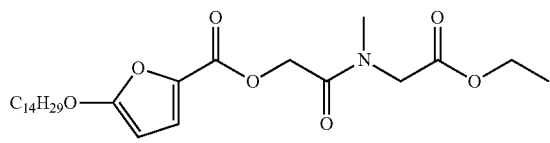

The title compound was prepared as in Example 20, Steps 1 and 2 starting with 0.307 g (2.0 mmol) of sarcosine ethyl ester hydrochloride and 0.160 mL (2 mmol) of chloroacetyl chloride except that the reaction mixture in Step 1 was diluted in EtOAc rather than hexanes. $^1$H NMR (300 MHz, CDCl$_3$) δ: 7.23 (d, 1H), 5.32 (d, 1H), 4.95 and 4.8 (2s of rotamers, 2H), 4.05-4.25 (m, 6H), 3.1 and 3.0 (2s of rotamers, 3H), 1.75 (p, 2H), 1.2-1.5 (m, 25H), 0.9 (t, 3H).

SYNTHETIC EXAMPLE 26

Synthesis of 2-oxo-2-(piperidin-1-yl)ethyl-5-(tetradecyloxy)furan-2-carboxylate

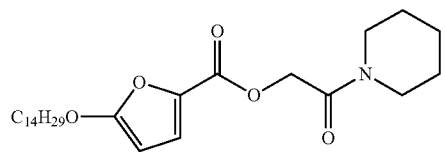

The title compound was prepared as in Example 20, Steps 1 and 2 starting with 0.198 mL (2.0 mmol) of piperidine and 0.160 mL (2 mmol) of chloroacetyl chloride except that the reaction mixture in Step 1 was diluted in EtOAc rather than hexanes. The crude material isolated in Step 2 was purified by recrystallization from isopropanol. $^1$H NMR (300 MHz, CDCl$_3$) δ: 7.22 (d, 1H), 5.35 (d, 1H), 4.87 (s, 2H), 4.15 (t, 2H), 3.55-3.6 (m, 2H), 3.3-3.4 (m, 2H), 1.75 (p, 2H), 1.5-1.7 (m, 6H), 1.2-1.5 (m, 22H), 0.9 (t, 3H).

SYNTHETIC EXAMPLE 27

Synthesis of 2-morpholino-2-oxoethyl 5-(tetradecyloxy)furan-2-carboxylate

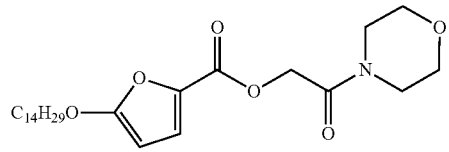

The title compound was prepared as in Example 20, Steps 1 and 2 starting with 0.157 mL (2.0 mmol) of morpholine and 0.160 mL (2 mmol) of chloroacetyl chloride except that the reaction mixture in Step 1 was diluted in EtOAc rather than hexanes. $^1$H NMR (300 MHz, CDCl$_3$) δ: 7.23 (d, 1H), 5.35 (d, 1H), 4.86 (s, 2H), 4.15 (t, 2H), 3.68-3.75 (m, 4H), 3.6-3.65 (m, 2H), 3.4-3.45 (m, 2H), 1.75 (p, 2H), 1.2-1.5 (m, 22H), 0.9 (t, 3H).

SYNTHETIC EXAMPLE 28

Synthesis of 2-(3,4-dihydroisoquinolin-2(1H)-yl)-2-oxoethyl 5-(tetradecyloxy)furan-2-carboxylate

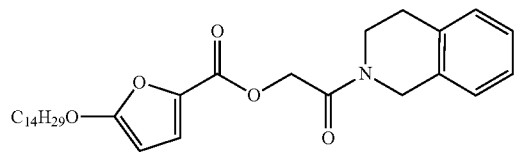

The title compound was prepared as in Example 20, Steps 1 and 2 starting with 0.339 g (2.0 mmol) of 1,2,3,4-tetrahydroisoquinoline hydrochloride and 0.160 mL (2 mmol) of chloroacetyl chloride except that the reaction mixture in Step 1 was diluted in a 1:1 mixture of hexanes:EtOAc rather than hexanes. $^1$H NMR (300 MHz, CDCl$_3$) δ: 7.05-7.25 (m, 5H), 5.32 (d, 1H), 4.95 (2s of rotamers, 2H), 4.65 and 4.7 (2s of rotamers, 2H), 4.15 (t, 2H), 3.83 and 3.63 (2t of rotamers, 2H), 2.92 and 2.85 (2t of rotamers, 2H), 1.78 (p, 2H), 1.2-1.5 (m, 22H), 0.9 (t, 3H).

SYNTHETIC EXAMPLE 29

Synthesis of (S)-benzyl 1-(2-(5-(tetradecyloxy)furan-2-carbonyloxy)acetyl)pyrrolidine-2-carboxylate

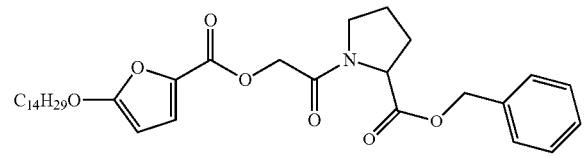

The title compound was prepared as in Example 20, Steps 1 and 2 starting with 0.483 g (2.0 mmol) of L-proline benzyl ester hydrochloride and 0.160 mL (2 mmol) of chloroacetyl chloride except that the reaction mixture in Step 1 was diluted in EtOAc rather than hexanes. The crude material isolated in Step 2 was purified by recrystallization from isopropanol. $^1$H NMR (300 MHz, CDCl$_3$) δ: 7.23-7.25 (m, 5H), 7.2 (d, 1H), 5.3 (d, 1H), 5.15 (d, 2H), 4.2-5.0 (m, 3H), 4.13 (t, 2H), 3.5-3.7 (m, 2H), 1.95-2.3 (m, 4H), 1.75 (p, 2H), 1.2-1.5 (m, 22H), 0.83 (t, 3H).

SYNTHETIC EXAMPLE 30

Synthesis of 4-methyl pentyl 5-(tetradecyloxy)furan-2-carboxylate

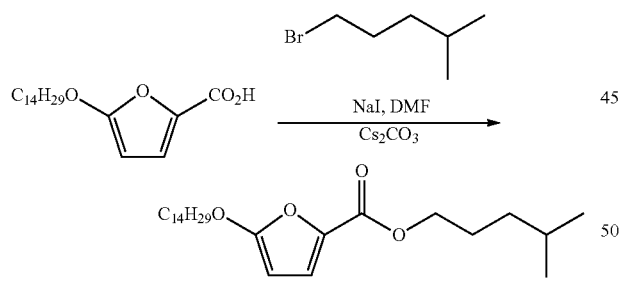

To a vigorously stirred suspension of 5-(tetradecyloxy) furan-2-carboxylic acid (0.162 g, 0.5 mmol) in 10 mL of N,N-dimethylformamide was added 1-bromo-4-methylpentane (0.247 g, 1.5 mmol), cesium carbonate (0.243 g, 0.75 mmol) and sodium iodide (~20 mg). The suspension appeared to go into solution briefly, and then a very finely dispersed white precipitate was observed. The reaction was allowed to stir for 12 hrs at which time HPLC analysis of the reaction solution indicated complete conversion of TOFA to a less polar product. The suspension was diluted with EtOAc (40 mL), brine (20 mL) and water (20 mL). The phases were separated and the organic phase was washed with water (20 mL) and brine (20 mL) and then dried and concentrated. The resulting crude material was purified by flash chromatography eluting with 0-20% EtOAc in hexanes to yield 0.127 g (62%) of the title compound. $^1$H NMR (300 MHz, CDCl$_3$) δ: 7.15 (d, 1H), 5.30 (d, 1H), 4.22 (t, 2H), 4.10 (t, 2H), 1.18-1.80 (m, 29H), 0.89 (t, 9H).

SYNTHETIC EXAMPLE 31

Synthesis of 3-(tetrahydro-2H-pyran-2-yloxy)propyl 5-(tetradecyloxy)furan-2-carboxylate

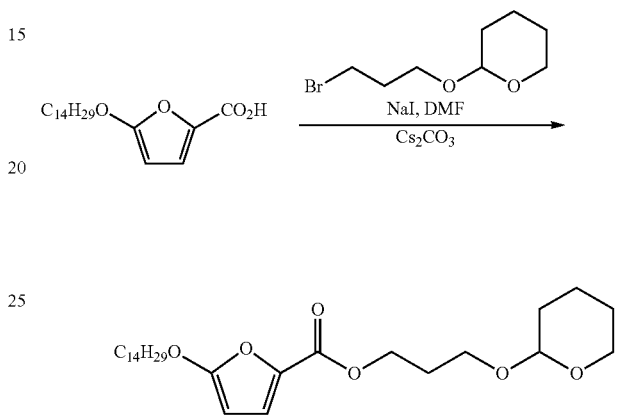

The title compound was prepared as in Example 30 starting with 0.335 g (1.5 mmol) of 2-(3-bromopropoxy)tetrahydro-2H-pyran and 0.162 g (0.5 mmol) of 5-(tetradecyloxy)furan-2-carboxylic acid. $^1$H NMR (300 MHz, CDCl$_3$) δ: 7.15 (d, 1H), 5.30 (d, 1H), 4.59-4.62 (m, 1H), 4.40 (app t, 2H), 4.10 (t, 2H), 3.80-3.90 (m, 2H), 3.40-3.60 (m, 2H), 2.05 (p, 2H), 1.20-1.85 (m, 30H), 0.89 (t, 3H).

SYNTHETIC EXAMPLE 32

Synthesis of 2-morpholinoethyl 5-(tetradecyloxy)furan-2-carboxylate

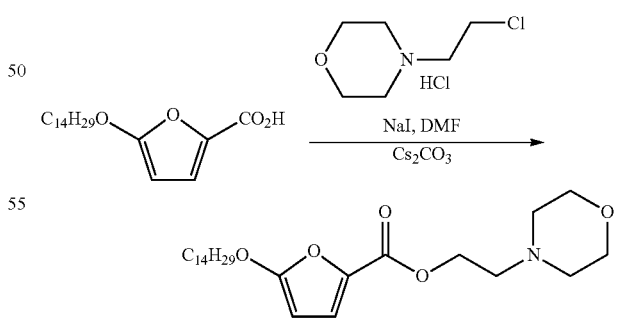

The title compound was prepared as in Example 30 starting with 0.224 g (1.2 mmol) of 4-(2-chloroethyl)morpholine hydrochloride and 0.162 g (0.5 mmol) of 5-(tetradecyloxy) furan-2-carboxylic acid with the exception that a total of 0.730 g of cesium carbonate was added to neutralize the hydrochloride. $^1$H NMR (300 MHz, CDCl$_3$) δ: 7.15 (d, 1H), 5.30 (d, 1H), 4.40 (t, 2H), 4.10 (t, 2H), 3.70 (app t, 4H), 2.70 (t, 2H), 2.55 (app t, 4H), 1.80 (p, 2H), 1.18-1.55 (m, 22H), 0.89 (t, 3H).

SYNTHETIC EXAMPLE 33

Synthesis of 2-(5-(tetradecyloxy)furan-2-carbonyloxy)benzoic acid

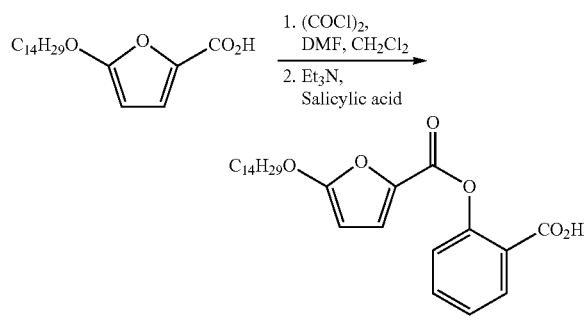

To a cooled (0° C.) and stirred suspension of 5-(tetradecyloxy)furan-2-carboxylic acid (0.324 g, 1 mmol) in 10 mL of $CH_2Cl_2$ was added oxalyl chloride (0.135 mL, 1.5 mmol) and 2 drops of N,N-dimethylformamide. Immediate effervescence was observed. The solution was allowed to warm to room temperature with continued stirring until such a time that gas evolution had ceased and all suspended solids had dissolved. The solution was then cooled to 0° C. once more and salicylic acid (0.180 g, 1.3 mmol) and $Et_3N$ (3 mL) were added to the rapidly stirred reaction. After stirring for 2 hrs, the reaction was diluted with EtOAc (100 mL) and the organic phase was washed with 1M HCl (2×100 mL) and brine (100 mL) and then dried and concentrated to give a white solid residue. The crude material was purified by flash chromatography eluting with 5-40% EtOAc in Hexanes with 1% AcOH. The resulting material was further purified by recrystallization from $CH_2Cl_2$ and hexanes to yield 0.225 g (57%) of the title compound as a white crystalline material. $^1H$ NMR (300 MHz, $CDCl_3$) δ: 8.08 (dd, 1H), 7.62 (dt, 1H), 7.32-7.38 (m, 2H), 7.24 (dd, 1H), 5.39 (d, 1H), 4.18 (t, 2H), 1.80 (p, 2H), 1.2-1.5 (m, 22H), 0.88 (t, 3H).

Testing of the Compounds of the Invention

Study of human sebocyte function has been relatively restricted due to the lack of suitable cell lines. Recently, SZ95 sebocytes were prepared using human facial sebaceous gland cells transfected with a plasmid containing the coding region for the Simian virus-40 large T antigen (see, Zouboulis, C. C. et al., *J. Invest. Dermatol.* (1999), Vol. 113, pp. 1011-1020). SZ95 cells express a number of molecules typically associated with human sebocytes. Functional studies showed synthesis of the sebaceous lipids squalene and wax esters as well as triglycerides and free fatty acids (see, Zouboulis C C, Seltmann H, Neitzel H, Orfanos C E. Establishment and characterization of an immortalized human sebaceous gland cell line (SZ95). *J. Invest Dermatol.* (1999) 113:1011-1020).

Thus, SZ95 cells are capable of recapitulating many aspects of sebocyte growth and differentiation (see, Wrobel, A. et al., "Differentiation and apoptosis in human immortalized sebocytes", *J. Invest Dermatol.* (2003) 120:175-181).

Treatment with arachidonic acid (AA) reproducibly increased SZ95 sebocyte lipid levels approximately 5-fold using a 96-well microtiter plate format. SZ95 cells can be used to identify compounds with sebum-inhibitory potential, such as Accutane® and cholesterol synthesis inhibitors (statins), both of which demonstrated the ability to lower lipid production by these cells (See, Tsukada, M. et al., "13-cis retinoic acid exerts its specific activity on human sebocytes through selective intracellular isomerization to all-trans retinoic acid and binding to retinoid acid receptors", *J. Invest. Dermatol.* (2000) 115:321-327).

The administration of compounds of the invention may also inhibit several parameters related to T cell activation including proliferation and secretion of immune/inflammation-regulating cytokines. Accordingly, analogs of TOFA would be useful agents in treating dermatological disorders or conditions characterized by inflammation, by reducing T cell proliferation and cytokine secretion, for example, in the treatment of inflammatory acne.

In vivo testing for evaluating potential acne treatment can be conducted using the following hamster assays because hamster ear sebaceous glands have a close resemblance to those of humans in terms of structure, biochemistry and physiology.

In Vivo Anti-Sebaceous Gland Activity Testing

The Syrian golden hamster (*Oryctolagus cuniculus*) ear sebaceous gland model was used to evaluate the effect of repeat application of TOFA and TOFA analogs. Male animals were employed since they have larger sebaceous glands than females a consequence of their higher endogenous levels of androgenic hormones. To define compound effects, cross-sections prepared from hamster ears were treated with the neutral lipid-specific stain Oil Red O. Staining results were compared to the untreated ear of the same animal in order to account for any changes in the overall physiological state of the animal as well as potential systemic effects stemming from local drug application.

Animal Treatment and Monitoring.

Typically, compounds were prepared and applied in 40% dimethyl acetamide (DMA)/30% acetone/30% ethanol (vehicle). Animals were typically 10-12 weeks of age and 100-150 g bodyweight at the start of the experiment. Treatment groups consisted of 5-8 animals. Non-anesthetized hamsters were administered the test material onto the ventral surface of the right ear using a pipette at a volume of 20 µl per ear. Materials were gently massaged into the treatment site with a gloved finger for approximately 15 sec. Hamsters received treatment once daily for 15-28 consecutive days. Application of the test articles occurred within the same 4-hour period on each application day. The left ear remained untreated and served as an internal control site. Animals were evaluated daily for general appearance and potential clinical signs related to treatment such as edema, erythema, discoloration or other changes to the ears. Hamsters were also assessed for general health by coat appearance, behavior, and activity level.

Sample Preparation for Histology.

Animals were euthanized by $CO_2$ asphyxiation approximately 16-20 h following the final (21st) application. Tissue samples for sebaceous gland analysis were subsequently taken by histology personnel. The right (treated) and left (untreated) ears were carefully removed from euthanized hamsters. A 3.5 mm punch biopsy of the treated ear was marked with a marking dye on the ventral surface. A punch biopsy of the untreated ear was marked with a separate tissue-marking dye on the ventral surface. Tissues were embedded in a labeled mold filled with "Neg 50" cryo-embedding medium and frozen on liquid nitrogen. These blocks were sequentially wrapped in Parafilm® then aluminum foil for storage at −70° C. until required.

Sebaceous Gland Analysis.

To assess sebaceous gland status, ear cross-sections were initially cut at a thickness of approximately 8 μm onto glass slides and immediately fixed with 10% buffered formalin. Sections were stained with the lipid-specific Oil Red O dye by standard methods, covered with Faramount (Dakocytomation, Ca) acrylic mounting medium, cover slipped and then allowed to set. A Tissue sections stained with Oil Red O were viewed with a Spot RT digital camera mounted on an Olympus BX60 microscope. Tissue sections stained with Oil Red O were viewed with a Spot RT digital camera mounted on an Olympus BX60 microscope. An image of the section was taken using the 4× microscope objective. The image was saved using the unique animal identification number, slide number, and magnification. Relative sebaceous gland areas (red staining areas) were determined using Image-Pro software (Media Cybernetics Inc., Silver Spring, Md.). The area of image analysis was the dermis which included the region from the epidermal-dermal junction to the midline of the tissue demarcated by the central cartilage line. Data was expressed as percentage of the area of the tissue cross section which was red in color, representative of lipid-containing structures, in comparison to the total area analyzed.

The following Biological Examples may be used by one skilled in the art to determine the effectiveness of the compounds of the invention in treating a human having a dermatological disorder or condition characterized by sebaceous gland hyperactivity, in inhibiting sebaceous gland activity in a human, or in reducing T cell proliferation and cytokine secretion.

BIOLOGICAL EXAMPLE 1

Inhibition of Lipid Synthesis in SZ95 Sebocytes

The immortalized human sebocyte cell line, SZ95, was maintained in culture as described in Zouboulis, C. C. et al., J. Invest. Dermatol. (1999), Vol. 113, pp. 1011-1020. Lipid synthesis was stimulated by treating SZ95 cells with arachidonic acid (AA). For measurement of lipid production and lipid inhibition studies, test compounds were dissolved in dimethylsulfoxide (DMSO) and added at the desired concentration in 96-well microtiter plates. The cells were then cultured for up to 72 hours before the plates were washed 3 times with PBS and a final volume of 200 μL PBS/well was added. To stain cell neutral lipids, 5 μL of Nile Red solution (0.2 mg/mL dissolved in DMSO) was added to each well and incubated for a minimum of 60 minutes. Plate fluorescence was then quantified using a fluorometric plate reader (excitation wavelength: 490 nm; emission wavelength: 590 nm). Inhibition of lipid levels by the test compound was expressed as the % reduction of the fluorescence of AA-stimulated cells in the presence of the test compound relative to the values obtained for the unstimulated control cells. Cell viability was measured by utilizing the conversion of a tetrazolium reagent (MTS) to a colored-formazan product by live cells. For these assays, the test compound was dissolved in dimethylsulfoxide (DMSO) and added at the desired concentration to cells seeded into 96-well plates. The cells were cultured for 48 hours in the presence of the test compound before the plates were washed 3 times with PBS. A final volume of 100 μL of culture medium per well was added. Twenty μL of MTS solution (0.2 mg/mL in sterile PBS) was added to each well and incubated for a minimum of 60 minutes until the desired optical density was reached. The color development of the wells was measured using a plate reader at an absorbance of 590 nm. Effect on cell viability by the test compound was expressed as the % reduction of the absorbance for AA-stimulated cells in the presence of the test compound relative to the values obtained for the untreated control cells.

Compounds of the invention, when tested in this assay, showed a dose-dependent inhibition of lipid synthesis.

BIOLOGICAL EXAMPLE 2

Effect of a Compound of the Invention on Lipid Accumulation by LNCaP Cells

The human prostate LNCaP adenocarcinoma cell line can be obtained from American Type Culture Collection. Cells are maintained in RPMI 1640 medium containing 10% fetal calf serum (FCS), 4 mM Glutamax, 1 mM sodium pyruvate, 1 mM HEPES, penicillin (100 U/mL) and streptomycin (100 μg/mL). For experiments, approximately 10,000 cells/well are plated in 6-well tissue culture plates in RPMI 1640 10% FBS for 72 hours. To minimize potential serum androgen effects, medium containing 5% charcoal/dextran-stripped FCS is added for 72 hours. Lipid synthesis is then stimulated by addition of the androgen dihydrotestosterone (DHT) at 50 nM. A compound of the invention is solubilized in DMSO and added at various concentrations in RPMI 1640 containing 5% charcoal/dextran-treated. Cells are incubated in the presence of these factors for 96 hours at 37° C. Lipid accumulation is subsequently quantified by Nile Red staining and flow cytometric analysis. The lipid level of test compound-treated wells is compared to the result obtained for the vehicle-treated cells.

BIOLOGICAL EXAMPLE 3

Effect of Compounds of the Invention on 3T3-L1 Adipocyte Differentiation and Lipid Accumulation Mouse 3T3-L1 preadipocytes (American Type Culture Collection) are passaged and maintained in Dulbecco's modified Eagles Medium (DMEM) supplemented with 10% fetal calf serum (FCS), 1 mM sodium pyruvate, penicillin (100 U/ml)/streptomycin (100 μg/ml) and 4 mM Glutamax (Gibco/Life Technologies). To initiate adipocyte differentiation, 3T3-L1 cells are plated at confluency into culture plates or dishes and grown in supplemented DMEM for two days post-confluency. Initiation medium consists of DMEM with 0.5 mM 3-isobutyl-1-methylxanthine, 1 μM dexamethasone and human insulin at 10 μg/ml. Progression medium contains insulin (10 μg/ml) which replaces the initiation medium after 48-72 hours. Cellular lipid is imaged by Oil Red O staining.

BIOLOGICAL EXAMPLE 4

Effect of a Compound of the Invention on Proliferation and Cytokine Production by Activated Human Peripheral Blood Mononuclear Cells (PBMC)

PBMC are isolated from different donors by density gradient centrifugation. Different amounts of a compound of the invention are added to PBMC cultures in the presence of two different stimuli sets. One activating stimulus is phytohemagglutinin (PHA), a plant-derived mitogen that stimulates proliferation and cytokine synthesis by T lymphocytes. These cell preparations are also activated using a combination of interferon-γ (IFN-γ) and lipopolysaccharide (LPS) to stimulate cytokine production by the monocyte fraction within PBMC preparations. Following a 48 hour culture period, cell supernatants are obtained for simultaneous determination of cytokine levels using a flow cytometry-based quantification method. Cytokine levels are interpolated from a standard curve generated in parallel. Cell viability is assessed using a colorimetric assay based on the conversion of 3-(4,5-dimethylthiazol-2-yl)-5-(3-carboxymethoxyphenyl)-2-(4-sulfophenyl)-2H-tetrazolium, inner salt (MTS) into a soluble formazan product by mitochondrial dehydrogenase of viable cells. Cell proliferation is determined by adding $^3$H-thymidine to the cultures and determining its level of incorporation into DNA using scintillation counting.

BIOLOGICAL EXAMPLE 5

Determination of Solubility in Synthetic Sebum

Compounds described herein can be tested to evaluate their solubility in lipids. To determine the solubility, a synthetic sebum mixture was used. More specifically, approximately 5 mg of a compound was added into 1.5 ml eppendorf tubes, which was then combined with 0.1 ml of synthetic sebum and then briefly vortexed. Mixtures were placed samples in a shaker pre-heated to 32° C. and then agitated overnight. Prior to sampling for HPLC analysis, tubes were placed in an eppendorf centrifuge and spun at 13000 rpm for 5 min to pellet the insoluble drug portion. Following centrifugation, 20 ul of the top portion of the soluble fraction was sampled, in triplicate, into a 2 ml HPLC vial for analysis and the mass recorded. One ml of THF was then added to each vial to solubilize sebum. To determine their concentrations, HPLC analysis of all compounds was carried out under the same running conditions.

The following compounds of the invention were tested in this assay:

2,2,2-trifluoroethyl 5-(tetradecyloxy)furan-2-carboxylate (Compound A);

isopropyl 5-(tetradecyloxy)furan-2-carboxylate (Compound B)

(5-methyl-2-oxo-1,3-dioxol-4-yl)methyl 5-(tetradecyloxy)furan-2-carboxylate (Compound C).

Table 1 shows that Compounds A, B and C exhibited considerably lower meting points and far greater solubility in liquid synthetic sebum than TOFA, which properties could promote their associations with the skin and delivery into the lipid-rich environment of the sebaceous glands.

TABLE 1

| Compound | Molecular weight (Daltons) | Melting Point (° C.) | Solubility in Liquid Synthetic Sebum (mg/ml) |
| --- | --- | --- | --- |
| TOFA | 324.5 | 119 | 1.5 ± 0.4 |
| Compound A | 406.5 | 37 | 28.9 ± 9.2 |
| Compound B | 366.5 | <22 | 43.0 ± 0.5 |
| Compound C | 436.5 | 35 | 13.6 ± 1.9 |

BIOLOGICAL EXAMPLE 6

In Vivo Assays

A series of hamster experiments were performed testing the potential anti-sebaceous gland activity of compounds of the invention in comparison to TOFA. In all experiments, repeat topical applications of TOFA and the compounds of the invention were well-tolerated. Neither erythema, edema, inflammation nor tissue necrosis was observed for treated as well as untreated ears of these animals. Hamsters exhibited normal behavior and weight gain through the duration of all experiments.

In these experiments, the compound of the invention, TOFA and vehicle were applied onto male hamster ears. At the end of treatment, the hamsters were sacrificed and the area of sebaceous glands in the treated area was determined. The untreated ear in this test system acted as an assay internal control as well as a means to detect potential systemic treatment effects.

This hamster assay evaluated the effect of topical application of TOFA in parallel with three compounds of the invention (Compounds A, B and C) on hamster ear sebaceous glands. Test compounds were applied topically daily at 75 mM for 21 days in 40% DMA/30% acetone/30% ethanol.

As shown in FIG. 1, compounds of the invention (in particular, Compound A), when tested in this assay, demonstrated the ability to reduce sebaceous gland area when compared to TOFA and when compared to vehicle.

BIOLOGICAL EXAMPLE 7

In Vivo Assays—Sustained Inhibitory Effects

Figure 2:
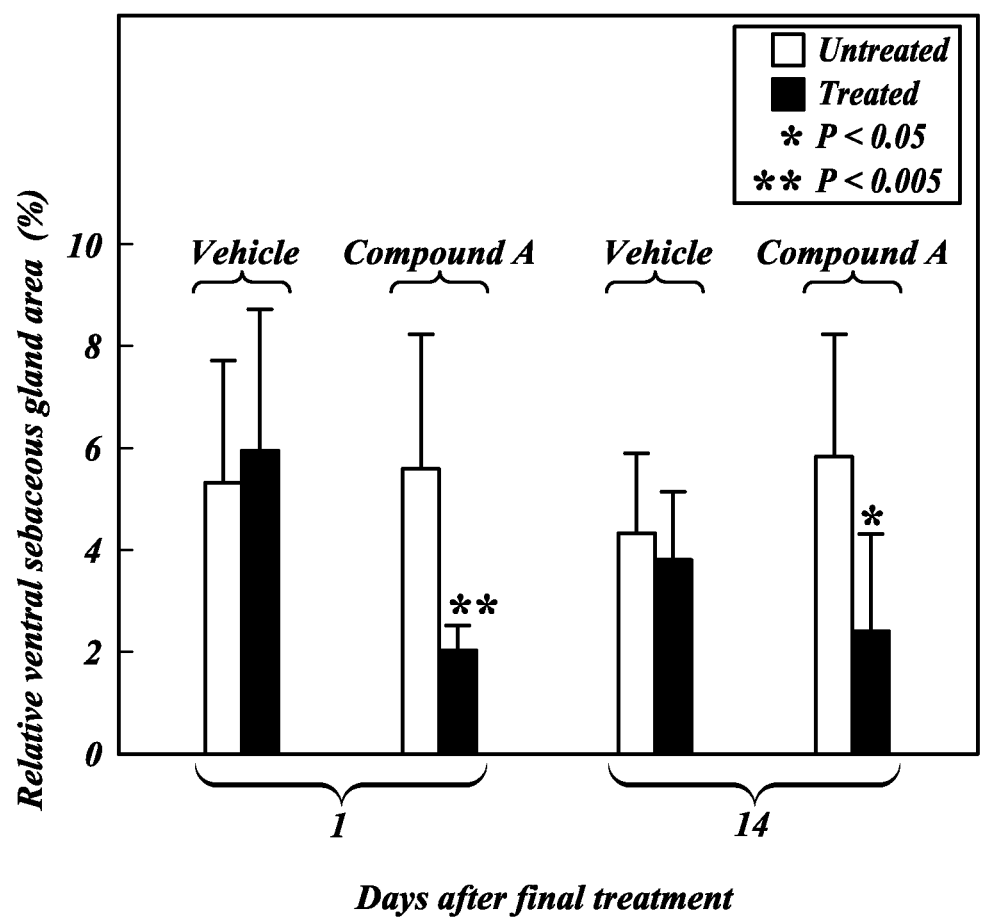
FIG. 2 shows the result of a further in vivo assay to assess hamster sebaceous gland size after 21 days of application of Compound A as well as one and two weeks following cessation of treatment. Mean sebaceous gland counts with standard deviations (7-8 animals per group at each time point) for untreated and treated ears are shown. *P<0.05; **P<0.005 as compared to solvent-treated animals.

This example assessed hamster sebaceous gland size after 21 days of application of Compound A as well as one and two weeks following cessation of treatment. Compound A was applied in a mixture of 40% DMA/30% acetone/30% ethanol. One-week and two-week follow-up sampling times were included to assess sebaceous gland recovery characteristics following the treatment. A significant reduction in gland size was again produced with 21 days of Compound A treatment (shown in FIG. 2). In comparison to vehicle-treated animals, average gland area was 63.5% lower for hamsters treated with Compound A. For samples prepared two weeks after completion of treatment, sebaceous gland counts for ears exposed to Compound A were significantly lower than control values. This finding suggests a relatively sustained inhibitory effect on gland activity following treatment of the TOFA analogs described herein. Moreover, the finding suggests that an exaggerated rebound effect may not occur after cessation of a treatment regimen.

BIOLOGICAL EXAMPLE 8

In Vivo Assays—Reduced Sebaceous Gland

Figure 3:
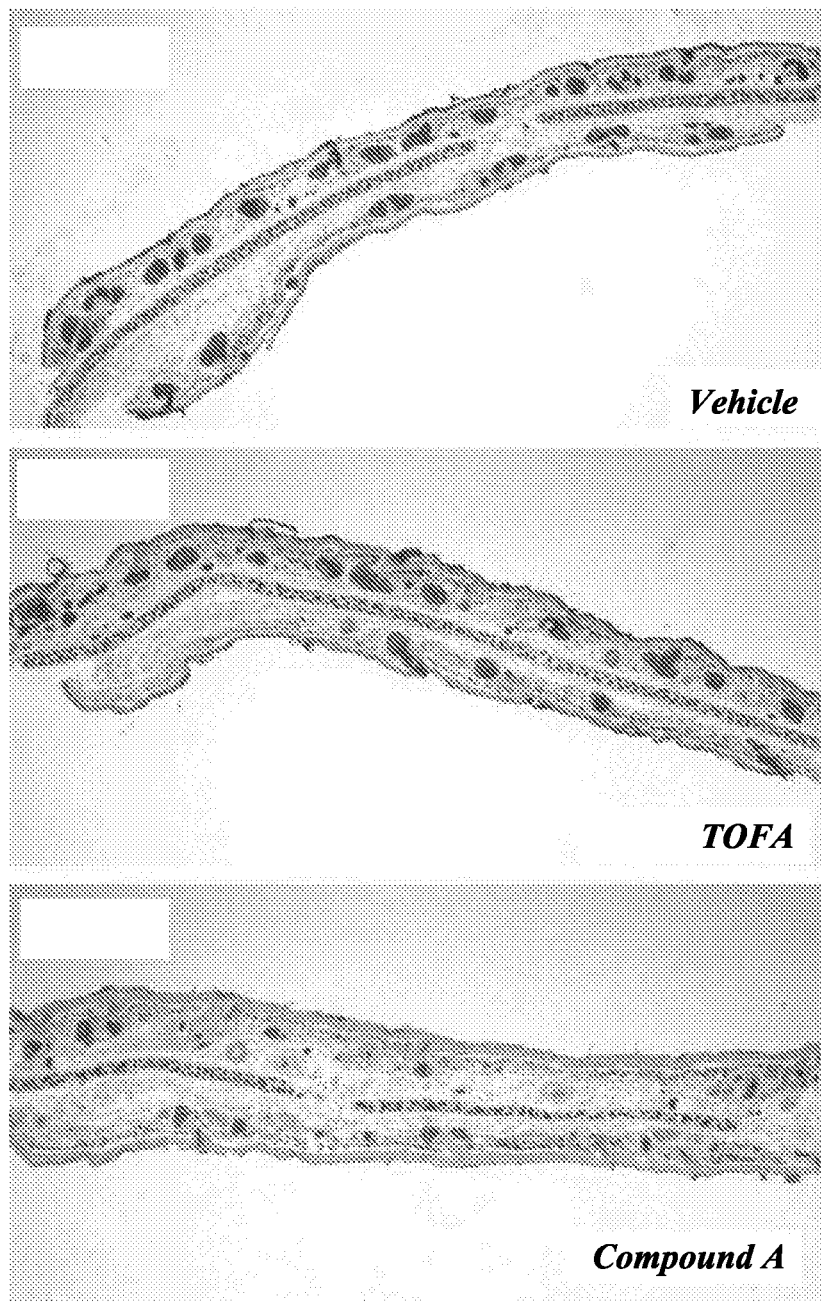
FIG. 3 shows the histological appearance of ear cross-sections prepared in a study in which animals were treated for 21 consecutive days with control vehicle (40% DMA/30% acetone/30% ethanol), TOFA and Compound A, respectively.

FIG. 3 shows the histological appearance of ear cross-sections prepared in a study in which animals were treated for 21 consecutive days with control vehicle (40% DMA/30% acetone/30% ethanol), TOFA and Compound A at a concentration of 75 mM in a mixture. No appreciable inflammatory cell presence evident for skin sections prepared from the ears of hamsters treated with the control, TOFA and Compound A.

Sections were treated with Oil Red O to detect neutral lipids and counter-stained with hematoxylin. Images are orientated with the ventral ear surface positioned upwards. Reduced sebaceous gland area is evident in the section prepared from a Compound A-treated hamster. In comparison to vehicle-treated controls, epidermal thickness is greater for samples obtained from hamsters treated with TOFA or Compound A.

Pharmaceutical Compositions of the Invention and Administration

Pharmaceutical compositions comprising a compound of the invention, or a pharmaceutically acceptable salt thereof, and a pharmaceutically acceptable excipient are one aspect of the present invention. These pharmaceutical compositions may be in any form which allows for the active ingredient, i.e., a compound of formula (I), to be administered to a human in a therapeutically effective amount. For example, the pharmaceutical composition may be in the form of a semi-solid (gel), solid, liquid or gas (aerosol). Typical routes of administration include, without limitation, systemic (including oral and parenteral), topical, buccal, transdermal, sublingual, nasal, rectal, vaginal, and intranasal administration. The term parenteral as used herein includes subcutaneous injections, needle-less injections, intravenous, intramuscular, epidural, intrasternal injection or infusion techniques. Pharmaceutical compositions of the invention are formulated so as to allow the active ingredients contained therein to be bioavailable upon administration of the composition to a human. Pharmaceutical compositions of the invention that will be administered to a human may take the form of one or more dosage units, where for example, a tablet, capsule, cachet or patch may be a single dosage unit, and a container of a pharmaceutical composition of the invention in aerosol form may hold a plurality of dosage units.

In treating dermatological disorders characterized by sebaceous gland hyperactivity, the compound of formula (I) is preferably administered to the skin (i.e., topically) of the human in need thereof in dermatologically acceptable compositions, as described in more detail below. When such compositions are in use (e.g., when a dermatological composition comprising a compound of formula (I) and a dermatologically acceptable excipient is placed upon the skin of the human in need thereof), the compound of formula (I) is in continuous contact with the skin of the patient, thereby effecting treatment.

Any suitable amount of a compound of formula (I) can be employed in such dermatological compositions, provided the amount employed effectively inhibits the production of sebum from sebocytes and remains stable in the composition over a prolonged period of time. Preferably, the stability is over a prolonged period of time, e.g., up to about 3 years, up to 1 year, or up to about 6 months, which is typical in the manufacturing, packaging, shipping and/or storage of dermatologically acceptable compositions. A compound of formula (I) can be in solution, partially in solution with an undissolved portion or completely undissolved suspension. A compound of formula (I) can be present in a dermatological composition of the invention in a concentration range from about 0.001 wt. % to about 80 wt. %, from about 0.001 wt. % to about 50 wt. %, from about 0.001 wt. % to about 25 wt. %, or from about 0.001 wt. % to about 6 wt. % of the dermatological composition. In one embodiment, a compound of formula (I) can be present in a concentration range of from about 0.001 wt. % to about 10 wt. %, from about 0.1 wt. % to about 10 wt. % or from about 1.0 wt. % to about 5.0 wt. % of the dermatological composition. In another embodiment of the invention, a dermatological formulation of a compound of formula (I) to be administered topically contains (by weight) about 3% TOFA in about 40% dimethylacetamide (DMA)/30% acetone/30% ethanol.

A dermatological composition of the invention can be in the form of a solution, lotion, foam, gel, cream and/or ointment. Preferably, the dermatological composition will be a topical formulation, for example, a gel, foam, cream or ointment.

A dermatological composition of the invention can contain one or more "lipophilic solvent(s)" that acts as a carrier into the pilosebaceous unit. A lipophilic solvent useful in the invention can be miscible with water and/or lower chain alcohols and have a vapor pressure less than water at 25° C. (~23.8 mm Hg). A lipophilic solvent useful in the invention can be a glycol, specifically propylene glycol. In particular, the propylene glycol can be from the class of polyethylene glycols, specifically polyethylene glycols ranging in molecular weight from 200 to 20000. Preferably, the solvent would be part of a class of glycol ethers. More specifically, a lipophilic solvent of the invention would be diethylene glycol monoethyl ether (transcutol). As used herein, "diethylene glycol monoethyl ether" ("DGME") or "transcutol" refers to 2-(2-ethoxyethoxy)ethanol {CAS NO 001893} or ethyoxydiglycol.

A dermatological composition of the invention can also contain one or more "filler(s)" that has a vapor pressure greater than or equal to 23.8 mm Hg at 25° C. The filler should have a vapor pressure greater than or equal to the lipophilic solvent as to concentrate the compound of formula (I) on the skin. Preferred concentration range of a single filler or the total of a combination of fillers can be from about 0.1 wt. % to about 10 wt. %, more preferably from about 10 wt. % to about 50 wt. %, more specifically from about 50 wt. % to about 95 wt. % of the dermatological composition. Non-limiting examples for use herein include water and lower alcohols, including ethanol, 2-propanol and n-propanol. More preferably, the filler is water, ethanol and/or 2-propanol. Specifically, the filler would be ethanol and/or water.

A dermatological composition of the invention can also contain one or more "humectant(s)" used to provide a moistening effect. Preferably the humectant remains stable in the composition. Any suitable concentration of a single humectant or a combination of humectants can be employed, provided that the resulting concentration provides the desired moistening effect. Typically, the suitable amount of humectant will depend upon the specific humectant or humectants employed. Preferred concentration range of a single humectant or the total of a combination of humectants can be from about 0.1 wt. % to about 70 wt. %, more preferably from about 5.0 wt. % to about 30 wt. %, more specifically from about 10 wt. % to about 25 wt. % of the dermatological composition. Non-limiting examples for use herein include glycerin, polyhydric alcohols and silicone oils. More preferably, the humectant is glycerin, propylene glycol and/or cyclomethicone. Specifically, the filler would be glycerine and/or cyclomethicone.

A dermatological composition of the invention can also contain a gelling agent that increases the viscosity of the final solution. The gelling agent can also act as an emulsifying agent. The present dermatogological compositions can form clear gels and soft gels, which upon application to the skin can break down and deteriorate, affording gels that do not dry on the skin. Typically, the concentration and combination of gelling agents will depend on the physical stability of the finished product. Preferred concentration range of a gelling agent can be from about 0.01 wt. % to about 20 wt. %, more preferably from about 0.1 wt. % to about 10 wt. %, more specifically from about 0.5 wt. % to about 5 wt. % of the dermatological composition. Non-limiting examples for use herein include classes of celluloses, acrylate polymers and acrylate crosspolymers. Preferably, hydroxypropyl cellulose, hydroxymethyl cellulose, Pluronic PF127 polymer, carbomer 980, carbomer 1342 and carbomer 940, more preferably hydroxypropyl cellulose, Pluronic PF127 carbomer 980 and carbomer 1342, more specifically hydroxypropyl cellulose (Klucel® EF, GF and/or HF), Pluronic PF127, carbomer 980 and/or carbomer 1342 (Pemulen® TR-1, TR-2 and/or Carbopol® ETD 2020).

A dermatological composition of the invention can contain one or more anti-oxidants, radical scavengers, and/or stabilizing agents, preferred concentration range from about 0.001 wt. % to about 0.1 wt. %, more preferably from about 0.1 wt. % to about 5 wt. % of the dermatological composition. Non-limiting examples for use herein include butylatedhydroxytoluene, butylatedhydroxyanisole, ascorbyl palmitate, citric acid, vitamin E, vitamin E acetate, vitamin E-TPGS, ascorbic acid, tocophersolan and propyl gallate. More specifically the anti-oxidant can be ascorbyl palmitate, vitamin E acetate, vitamin E-TPGS, vitamin E or butylatedhydroxytoluene.

A dermatological composition of the invention can also contain preservatives that exhibit anti-bacterial and/or anti-fungal properties. Preservatives can be present in a gelled dermatological composition of the invention to minimize bacterial and/or fungal over its shelf-life. Preferred concentration range of preservatives in a dermatological composition of the invention can be from about 0.001 wt. % to about 0.01 wt. %, more preferably from about 0.01 wt. % to about 0.5 wt. % of the dermatological composition. Non-limiting examples for use herein include diazolidinyl urea, methylparaben, propylparaben, tetrasodium EDTA, and ethylparaben. More specifically the preservative would be a combination of methylparaben and propylparaben.

A dermatological composition can optionally include one or more chelating agents. As used herein, the term "chelating agent" or "chelator" refers to those skin benefit agents capable of removing a metal ion from a system by forming a complex so that the metal ion cannot readily participate in or catalyze chemical reactions. The chelating agents for use herein are preferably formulated at concentrations ranging from about 0.001 wt. % to about 10 wt. %, more preferably from about 0.05 wt. % to about 5.0 wt. % of the dermatological composition. Non-limiting examples for use herein include EDTA, disodium edeate, dipotassium edeate, cyclodextrin, trisodium edetate, tetrasodium edetate, citric acid, sodium citrate, gluconic acid and potassium gluconate. Specifically, the chelating agent can be EDTA, disodium edeate, dipotassium edate, trisodium edetate or potassium gluconate.

The dermatological compositions of this invention can be provided in any cosmetically suitable form, preferably as a lotion or a cream, but also in an ointment or oil base, as well as a sprayable liquid form (e.g., a spray that includes TOFA in a base, vehicle or carrier that dries in a cosmetically acceptable way without the greasy appearance that a lotion or ointment would have when applied to the skin).

In addition, the dermatological compositions of the invention can include one or more compatible cosmetically acceptable adjuvants commonly used, such as colorants, fragrances, emollients, humectants and the like, as well as botanicals, such as aloe, chamomile and the like.

In topically administering the dermatological compositions of the invention, the skin of the human to be treated can be optionally pre-treated (such as washing the skin with soap and water or cleansing the skin with an alcohol-based cleanser) prior to administration of the dermatological composition of the invention.

In treating dermatological disorders or conditions characterized by sebaceous gland hyperactivity, a compound of formula (I) or a pharmaceutical composition comprising a compound of formula (I) can also be administered systemically, preferably orally, to the human in need thereof in pharmaceutically acceptable compositions, as described in more detail below.

A pharmaceutical composition of the invention to be orally administered can be prepared by combining a compound of formula (I) with an appropriate pharmaceutically acceptable carrier, diluent or excipient by standard methods known to one skilled in the art. Pharmaceutical compositions of the invention are formulated so as to allow the compound of formula (I) contained therein to be bioavailable upon administration of the composition to a human.

A pharmaceutical composition of the invention to be orally administered may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When a pharmaceutical composition of the invention is in the form of a capsule, for example, a gelatin capsule, it may contain, in addition to materials of the above type, a liquid carrier such as polyethylene glycol or oil.

A pharmaceutical composition of the invention to be orally administered may also be in the form of a liquid, for example, an elixir, syrup, solution, emulsion or suspension. The pharmaceutical composition may also optionally contain one or more of a sweetening agent, preservatives, dye/colorant and flavor enhancer.

Liquid pharmaceutical compositions of the invention may also include one or more of the following adjuvants: sterile water, saline solution (preferably physiological saline solution), Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose.

A liquid pharmaceutical composition of the invention contains a therapeutically effective amount of a compound of formula (I) when administered to a human in need thereof. Typically, this amount is at least 0.01% of a compound of formula (I) in the composition. This amount may be varied to be between about 0.1 wt. % and about 70% of the total weight of the composition. Preferred oral pharmaceutical compositions contain a compound of formula (I) at a concentration range of between about 1.0 wt. % and about 50 wt. % of the oral composition.

A pharmaceutical composition of the invention may include various materials, which modify the physical form of a solid or liquid dosage unit. For example, the composition may include materials that form a coating shell around the active ingredient. The materials that form the coating shell are typically inert, and may be selected from, for example, sugar, shellac, and other enteric coating agents. Alternatively, the active ingredient may be encased in a gelatin capsule.

A pharmaceutical composition of the invention in solid or liquid form may also include an agent that binds to a compound of formula (I) and thereby assists in the systemic delivery of the compound of formula (I). Suitable agents that may act in this capacity include a monoclonal or polyclonal antibody, a protein or a liposome.

Systemic administration of the pharmaceutical compositions of the invention also include administration by injection, e.g., subcutaneous, intravenous, intramuscular, intrathecal or intraperitoneal injection, as well as transdermal, transmucosal, or pulmonary administration and needle-less injection administration.

Useful injectable pharmaceutical compositions include sterile suspensions, solutions or emulsions of the active compound(s) in aqueous or oily vehicles. The compositions may also contain formulating agents, such as suspending, stabilizing and/or dispersing agent. The pharmaceutical compositions for injection may be presented in unit dosage form, e.g., in ampules or in multidose containers, and may contain added preservatives.

Alternatively, the injectable pharmaceutical compositions may be provided in powder form for reconstitution with a suitable vehicle, including but not limited to sterile pyrogen free water, buffer, dextrose solution, etc., before use. To this end, the active compound, i.e., a compound of formula (I), may be dried by any art-known technique, such as lyophilization, and reconstituted prior to use.

For transmucosal administration, penetrants appropriate to the barrier to be permeated are used in the formulation. Such penetrants are known in the art.

For prolonged delivery, a compound of formula (I), or a pharmaceutically acceptable salt thereof, can be formulated as a depot preparation for administration by implantation or intramuscular injection. A compound of formula (I), or a pharmaceutically acceptable salt thereof, may be formulated with suitable polymeric or hydrophobic materials (e.g., as an emulsion in an acceptable oil) or ion exchange resins, or as sparingly soluble derivatives, e.g., as a sparingly soluble salt. Alternatively, transdermal delivery systems manufactured as an adhesive disc or patch which slowly releases a compound of formula (I), or a pharmaceutically acceptable salt thereof, for percutaneous absorption may be used. To this end, permeation or penetration enhancers may be used to facilitate transdermal penetration of the active compound(s). Suitable transdermal patches are described in for example, U.S. Pat. No. 5,407,713; U.S. Pat. No. 5,352,456; U.S. Pat. No. 5,332,213; U.S. Pat. No. 5,336,168; U.S. Pat. No. 5,290,561; U.S. Pat. No. 5,254,346; U.S. Pat. No. 5,164,189; U.S. Pat. No. 5,163,899; U.S. Pat. No. 5,088,977; U.S. Pat. No. 5,087,240; U.S. Pat. No. 5,008,110; and U.S. Pat. No. 4,921,475.

Administration of the pharmaceutical compositions of the invention by needle-less injection can be employed using the techniques disclosed in U.S. Pat. No. 6,756,053.

Alternatively, other pharmaceutical delivery systems may be employed for the pharmaceutical compositions of the invention. Liposomes and emulsions are well-known examples of delivery vehicles that may be used to deliver active compound(s) or prodrug(s). Certain organic solvents such as dimethylsulfoxide (DMSO) may also be employed, although usually at the cost of greater toxicity.

The pharmaceutical compositions of the invention may, if desired, be presented in a pack or dispenser device which may contain one or more unit dosage forms containing the active compound(s). The pack may, for example, comprise metal or plastic foil, such as a blister pack. The pack or dispenser device may be accompanied by instructions for administration.

The pharmaceutical compositions of the invention as set forth above may be prepared by methodology well known in the pharmaceutical art or by the method described herein. See, for example, *Remington's Pharmaceutical Sciences*, 18th Ed., (Mack Publishing Company, Easton, Pa., 1990).

The pharmaceutical compositions of the invention are administered to a human in a therapeutically effective amount, which will vary depending upon a variety of factors including the activity of the compound of formula (I); the metabolic stability and length of action of the compound of formula (I); the age, body weight, general health, sex, and diet of the human; the mode and time of administration; the rate of excretion; the drug combination; and the severity of the particular disorder or condition. Generally, a therapeutically effective daily dose of a compound of formula (I) is (for a 70 kg mammal) from about 0.001 mg/kg (i.e., 0.07 mg) to about 100 mg/kg (i.e., 7.0 gm); preferably a therapeutically effective dose is (for a 70 kg mammal) from about 0.01 mg/kg (i.e., 0.7 mg) to about 50 mg/kg (i.e., 3.5 gm); more preferably a therapeutically effective dose is (for a 70 kg mammal) from about 1 mg/kg (i.e., 70 mg) to about 25 mg/kg (i.e., 1.75 gm).

The following Formulation Examples 1-5 provide dermatological compositions of the invention comprising a representative compound of formula (I) and one or more dermatologically acceptable excipients.

FORMULATION EXAMPLE 1

Dermatological Alcoholic Gel Formulation

The product of the following formulation is a semi-solid clear gel.

| Ingredient | Percent w/w |
|---|---|
| Compound of formula (I) | 1.0 |
| Diethylene Glycol Monoethyl Ether, NF | 32.0 |
| Tocophersolan, NF | 1.0 |
| Hydroxypropyl Cellulose, NF (Klucel ® GF) | 4.0 |
| Edetate Disodium | 0.05 |
| Alcohol, Dehydrated, NF | 61.95 |

The above formulation may be prepared as follows. The alcohol and diethylene glycol monoethyl ether are combined. Tocophersolan, edetate disodium and the compound of formula (I) are dissolved with mixing. Hydroxypropyl cellulose is added and quickly and evenly dispersed with high-speed mixing. The product is removed from mixing after uniform dispersion.

FORMULATION EXAMPLE 2

Dermatological Aqueous Gel Formulation

The product of the following formulation is a semi-solid clear soft gel.

| Ingredient | Percent w/w |
|---|---|
| Compound of formula (I) | 1.0 |
| Diethylene Glycol Monoethyl Ether, NF | 30.0 |
| Glycerin, USP | 5.0 |
| Tocophersolan, NF | 1.0 |
| Methylparaben, NF | 0.1 |
| Propylparaben, NF | 0.02 |

| Ingredient | Percent w/w |
| --- | --- |
| Edetate Disodium | 0.05 |
| Acrylates/C10-C30 Alkyl Acrylate Crosspolymer, NF | 2.0 |
| Polysorbate 80, NF | 0.1 |
| Trolamine, NF | to pH 6.75 |
| Water, USP | to 100.0 |

The above formulation may be prepared as follows. The liquids, diethylene glycol monoethyl ether, glycerin and water, are mixed. Polysorbate 80 and tocophersolan are added and mixed to dissolve. The compound of formula (I) is added and mixed to dissolve. Edetate disodium, methylparaben, and propylparaben are added and mixed to dissolve. Acrylates/C10-C30 alkyl acrylate crosspolymer are quickly dispersed with high-speed mixing until uniform mixture obtained. Trolamine is added with constant mixing to obtain a viscous gel at a pH of approximately 6.75 (when diluted 1:9 with water).

FORMULATION EXAMPLE 3

Dermatological Hydroalcoholic Gel Formulation

The product of the following formulation is a semi-solid clear soft gel.

| Ingredient | Percent w/w |
| --- | --- |
| Compound of formula (I) | 1.0 |
| Diethylene Glycol Monoethyl Ether, NF | 30.0 |
| Alcohol, NF | 25.0 |
| Glycerin, USP | 5.0 |
| Tocophersolan, NF | 1.0 |
| Methylparaben, NF | 0.1 |
| Propylparaben, NF | 0.02 |
| Edetate Disodium | 0.05 |
| Hydroxypropyl Cellulose, NF (Klucel ® EF) | 2.0 |
| Acrylates/C10-C30 Alkyl Acrylate Crosspolymer, NF | 1.0 |
| Polysorbate 80, NF | 0.05 |
| Trolamine, NF | to pH 6.75 |
| Water, USP | to 100.0 |

The above formulation may be prepared as follows. The liquids, diethylene glycol monoethyl ether, glycerin alcohol and water, are mixed. Polysorbate 80 and tocophersolan are added and mixed to dissolve. The compound of formula (I) is added and mixed to dissolve. Edetate disodium, methylparaben and propylparaben are added and mixed to dissolve. Acrylates/C10-C30 alkyl acrylate crosspolymer and hydroxypropyl cellulose are quickly dispersed with high-speed mixing until uniform mixture obtained. Trolamine is added with constant mixing to obtain a viscous gel at a pH of approximately 6.75 (when diluted 1:9 with water).

FORMULATION EXAMPLE 4

Dermatological Cream Formulation

A compound of formula (I) may also be formulated as a cream, an example of which is as follows:

| Ingredient | Percent w/w |
| --- | --- |
| Compound of formula (I) | 1.0 |
| Diethylene Glycol Monoethyl Ether, NF | 20.0 |
| White Petrolatum | 5.0 |
| Isopropyl Myristate | 5.0 |
| Cetostearyl Alcohol | 5.0 |
| Trilaureth-4 Phosphate | 1.0 |
| Tocophersolan, NF | 1.0 |
| Cyclomethicone, NF | 5.0 |
| Methylparaben, NF | 0.2 |
| Propylparaben, NF | 0.04 |
| Edetate Disodium | 0.05 |
| Carbomer 940 | 0.15 |
| Acrylates/C10-C30 Alkyl Acrylate Crosspolymer, NF | 0.15 |
| Trolamine, NF | to pH 6.75 |
| Water, USP | to 100.0 |

The above formulation may be prepared as follows:

A. Water Phase

Water and diethylene glycol monoethyl ether are mixed together. Tocophersolan is added and mixed to dissolve. The compound of formula (I) is added and mixed to dissolve. Trilaureth-4 phosphate, edetate disodium, methylparaben and propylparaben are added and mixed to dissolve. Acrylates/C10-C30 alkyl acrylate crosspolymer and carbomer 940 are quickly dispersed with high-speed mixing until uniform mixture obtained. The resulting mixture is heated, while stirring, at a temperature of between about 65° C. and about 75° C. to form a solution.

B. Oil Phase

White petrolatum, cyclomethicone, isopropyl myristate and cetostearyl alcohol are combined in a separate vessel and melted completely at a temperature of between about 65° C. and about 75° C. and stirred.

C. While stirring the water phase, the oil phase is slowly added until a uniform emulsion is obtained. Trolamine is slowly added to the resulting emulsion to obtain a cream at a pH of approximately 6.75. The product is cooled to 25° C. with continuous mixing.

FORMULATION EXAMPLE 5

Dermatological Foam Formulation

A compound of formula (I) may also be formulated as a foam, an example of which is as follows:

| Ingredient | Percent w/w* |
| --- | --- |
| Compound of formula (I) | 1.0 |
| Diethylene Glycol Monoethyl Ether, NF | 25.0 |
| Stearyl Alcohol, NF | 8.0 |
| Laureth-23 | 0.5 |
| PEG-100 Stearate | 1.0 |
| Tocophersolan, NF | 1.0 |
| Propylparaben, NF | 0.3 |
| Edetate Disodium | 0.05 |
| Acrylates/C10-C30 Alkyl Acrylate Crosspolymer, NF | 0.2 |
| Trolamine, NF | to pH 6.75 |
| Water, USP | to 100.0 |

*Propellant is 4.0 wt. % of final formulation. The propellant is a single gas or a mixture of gases. Suitable gases include butane, isobutane, propane, isopropane and isopentate.

The above formulation may be prepared as follows:

A. Water Phase

Water and diethylene glycol monoethyl ether are mixed. Tocophersolan is added and mixed to dissolve. TOFA is added and mixed to dissolve. Edetate disodium and propylparaben are added and mixed to dissolve. Acrylates/C10-C30 alkyl acrylate crosspolymer is quickly dispersed with high-speed mixing until uniform mixture obtained. The resulting mixture is heated, while stirring, to solution at a temperature of between about 60° C. and about 70° C.

B. Oil Phase

Stearyl alcohol, laureth-23 and PEG-100 stearate are combined in a separate vessel and melted completely, while stirring, at a temperature of between about 60° C. and about 70° C.

C. While stirring the water phase, the oil phase is added until a uniform emulsion is obtained. Trolamine is added to afford the desired pH. The resulting formulation is cooled to 25° C. with continuous mixing. The formulation is packaged in an appropriate air-tight container under pressure with propellant.

Combination Therapy

Compounds of the invention may be usefully combined with one or more other therapeutic agents in the treatment of dermatological disorders or conditions characterized by sebaceous gland hyperactivity. For example, a compound of the invention may be administered simultaneously, sequentially or separately in combination with other therapeutic agents, including, but not limited to:

topical/oral antibiotics, e.g., clindamycin, tetracycline, minoccline, deoxycycline, erythromycin, trimethoprim, and azithromycin;
retinoids, e.g., Accutane®, tretinion, tazarotene, and adapalene;
benzoyl peroxide;
blue/red light;
photodynamic therapy (PDT);
Anti-androgenic compounds, e.g., PSK 3841;
5-alpha reductase type I inhibitors;
comedolytics, e.g., salicylic acid, azelaic acid, sulfur and resorcinol.

As used herein "combination" refers to any mixture or permutation of a compound of the invention and one or more additional therapeutic agents useful in the treatment of dermatological disorders or conditions. Unless the context makes clear otherwise, "combination" may include simultaneous or sequentially delivery of a compound of the invention with one or more therapeutic agents. Unless the context makes clear otherwise, "combination" may include dosage forms of a compound of the invention (e.g., dermatological or pharmaceutical compositions comprising a compound of the invention and a dermatological acceptable excipient) with another therapeutic agent. Unless the context makes clear otherwise, "combination" may include routes of administration of a compound of the invention with another therapeutic agent. Unless the context makes clear otherwise, "combination" may include compositions comprising a compound of the invention and another therapeutic agent. Dosage forms, routes of administration and dermatological and pharmaceutical compositions include, but are not limited to, those described herein.

All of the U.S. patents, U.S. patent application publications, U.S. patent applications, foreign patents, foreign patent applications and non-patent publications referred to in this specification are incorporated herein by reference in their entireties.

Although the foregoing invention has been described in some detail to facilitate understanding, it will be apparent that certain changes and modifications may be practiced within the scope of the appended claims. Accordingly, the described embodiments are to be considered as illustrative and not restrictive, and the invention is not to be limited to the details given herein, but may be modified within the scope and equivalents of the appended claims.

What is claimed is:

1. A compound of formula (I):

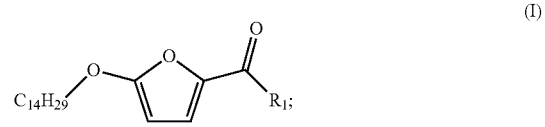

wherein:
$R^1$ is —O—$R^2$; and
$R^2$ is haloalkyl or aryl optionally substituted with —COOH,
as a single stereoisomer or as a mixture thereof;
or a pharmaceutically acceptable salt thereof.

2. The compound of claim 1 selected from:
2,2,2-trifluoroethyl 5-(tetradecyloxy)furan-2-carboxylate;
2,2,2-trichloroethyl 5-(tetradecyloxy)furan-2-carboxylate;
2-bromoethyl 5-(tetradecyloxy)furan-2-carboxylate; and
2-(5-(tetradecyloxy)furan-2-carbonyloxy)benzoic acid.

3. A compound of formula (I):

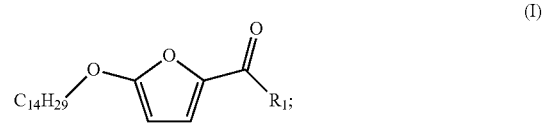

wherein:
$R^1$ is —O—$R^3$—C(O)N($R^5$)$R^6$;
$R^3$ is an alkylene chain; and
$R^4$ is alkyl, aryl, aralkyl, heteroaryl or heteroarylalkyl;
$R^5$ is hydrogen, alkyl, cycloalkyl, aryl or aralkyl; and
$R^6$ is alkyl, cycloalkyl, aralkyl or —$R^3$—C(O)O$R^4$;
or $R^5$ and $R^6$, together with the nitrogen to which they are both attached, form an N-heterocyclyl or N-heteroaryl, each of which being optionally substituted with cycloalkyl, aryl or —C(O)O$R^4$.

4. The compound of claim 3 selected from:
2-(benzyl(methyl)amino)-2-oxoethyl 5-(tetradecyloxy)furan-2-carboxylate;
tert-butyl 4-(2-(5-tetradecyloxy)furan-2-carbonyloxy)acetyl)piperazine-1-carboxylate;
2-(dicyclohexylamino)-2-oxoethyl 5-(tetradecyloxy)furan-2-carboxylate;
2-(4-cyclohexylpiperazin-1-yl)-2-oxoethyl 5-(tetradecyloxy)furan-2-carboxylate;
2-oxo-2-(4-phenylpiperzin-1-yl)ethyl-5-(tetradecyloxy)furan-2-carboxylate;
2-((2-ethoxy-2-oxoethyl)(methyl)amino)-2-oxoethyl 5-tetradecyloxy)furan-2-carboxylate;
2-oxo-2-(piperidin-1-yl)ethyl-5-(tetradecyloxy)furan-2-carboxylate;
2-morpholino-2-oxoethyl 5-(tetradecyloxy)furan-2-carboxylate;
2-(3,4-dihydroisoquinolin-2(1H)-yl)-2-oxoethyl 5-(tetradecyloxy)furan-2-carboxylate; and
(S)-benzyl 1-(2-(5-(tetradecyloxy)furan-2-carbonyloxy)acetyl)pyrrolidine-2-carboxylate.

5. A pharmaceutical composition comprising:
a compound of formula (I):

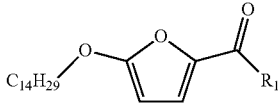 (I)

wherein,
R¹ is —O—R²; and
R² is haloalkyl or aryl optionally substituted with —COOH,
as a single stereoisomer or as a mixture thereof, or a pharmaceutically acceptable salt thereof; and
a pharmaceutically or dermatologically acceptable excipient.

6. The pharmaceutical composition of claim 5 wherein the compound of Formula (I) is:
2,2,2-trifluoroethyl 5-(tetradecyloxy)furan-2-carboxylate;
2,2,2-trichloroethyl 5-(tetradecyloxy)furan-2-carboxylate;
2-bromoethyl 5-(tetradecyloxy)furan-2-carboxylate; and
2-(5-(tetradecyloxy)furan-2-carbonyloxy)benzoic acid.

7. The pharmaceutical composition of claim 5 being a dermatological composition.

8. A pharmaceutical composition comprising:
a compound of formula (I):

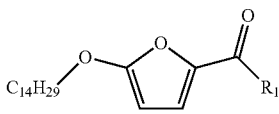 (I)

wherein:
R¹ is —O—R³—C(O)N(R⁵)R⁶;
R³ is an alkylene chain; and
R⁴ is alkyl, aryl, aralkyl, heteroaryl or heteroarylalkyl;
R⁵ is hydrogen, alkyl, cycloalkyl, aryl or aralkyl; and
R⁶ is alkyl, cycloalkyl, aralkyl or —R³—C(O)OR⁴;
or R⁵ and R⁶, together with the nitrogen to which they are both attached, form an N-heterocyclyl or N-heteroaryl, each of which being optionally substituted with cycloalkyl, aryl or —C(O)OR⁴;
as a single stereoisomer or as a mixture thereof, or a pharmaceutically acceptable salt thereof; and
a pharmaceutically or dermatologically acceptable excipient.

9. The pharmaceutical composition of claim 8 wherein the compound of Formula (I) is:
2-(benzyl(methyl)amino)-2-oxoethyl 5-(tetradecyloxy)furan-2-carboxylate;
tert-butyl 4-(2-(5-tetradecyloxy)furan-2-carbonyloxy)acetyl)piperazine-1-carboxylate;
2-(dicyclohexylamino)-2-oxoethyl 5-(tetradecyloxy)furan-2-carboxylate;
2-(4-cyclohexylpiperazin-1-yl)-2-oxoethyl 5-(tetradecyloxy)furan-2-carboxylate;
2-oxo-2-(4-phenylpiperzin-1-yl)ethyl-5-(tetradecyloxy)furan-2-carboxylate;
2-((2-ethoxy-2-oxoethyl)(methyl)amino)-2-oxoethyl 5-tetradecyloxy)furan-2-carboxylate;
2-oxo-2-(piperidin-1-yl)ethyl-5-(tetradecyloxy)furan-2-carboxylate;
2-morpholino-2-oxoethyl 5-(tetradecyloxy)furan-2-carboxylate;
2-(3,4-dihydroisoquinolin-2(1H)-yl)-2-oxoethyl 5-(tetradecyloxy)furan-2-carboxylate; and
(S)-benzyl 1-(2-(5-(tetradecyloxy)furan-2-carbonyloxy)acetyl)pyrrolidine-2-carboxylate.

10. The pharmaceutical composition of claim 8 being a dermatological composition.

11. A dermatological composition comprising 2,2,2-trifluoroethyl 5-(tetradecyloxy)furan-2-carboxylate and a dermatologically acceptable excipient.

12. A dermatological composition comprising tert-butyl 4-(2-(5-tetradecyloxy)furan-2-carbonyloxy)acetyl)piperazine-1-carboxylate and a dermatologically acceptable excipient.

13. A dermatological composition comprising 2-((2-ethoxy-2-oxoethyl)(methyl)amino)-2-oxoethyl 5-tetradecyloxy)furan-2-carboxylate and a dermatologically acceptable excipient.

* * * * *

UNITED STATES PATENT AND TRADEMARK OFFICE
CERTIFICATE OF CORRECTION

PATENT NO. : 8,884,034 B2  
APPLICATION NO. : 13/382138  
DATED : November 11, 2014  
INVENTOR(S) : Timothy Scott Daynard et al.

It is certified that error appears in the above-identified patent and that said Letters Patent is hereby corrected as shown below:

In the Claims

Column 54, Line 39, Claim 1:
"$R^3$ is an alkylene chain; and" should read, --$R^3$ is an alkylene chain;--.

Column 55, Line 25, Claim 6:
"2-bromethyl 5-(tetradecyloxy)furan-2-carboxylate; and" should read,
--2-bromethyl 5-(tetradecyloxy)furan-2-carboxylate; or--.

Column 55, Line 41, Claim 8:
"$R^3$ is an alkylene chain; and" should read, --$R^3$ is an alkylene chain;--.

Column 56, Line 4, Claim 8:
"with cycloalkyl, aryl or -C(O)OR$^4$;" should read, --with cycloalkyl, aryl or -C(O)OR$^4$,--.

Column 56, Lines 27-28, Claim 9:
"2-(3,4-dihydroisoquinolin-2(1H)-yl)-2-oxoethyl 5-(tetradecyloxy)furan-2-carboxylate; and" should read, --2-(3,4-dihydroisoquinolin-2(1*H*)-yl)-2-oxoethyl 5-(tetradecyloxy)furan-2-carboxylate; or--.

Signed and Sealed this  
Twenty-fourth Day of March, 2015

Michelle K. Lee  
*Director of the United States Patent and Trademark Office*